(12) United States Patent
Boucher et al.

(10) Patent No.: US 12,390,161 B2
(45) Date of Patent: Aug. 19, 2025

(54) DEVICES FOR AT-HOME PHYSICAL EXAMINATION OF THE EAR AND EAR CANAL

(71) Applicant: Zipline Health, Inc., San Francisco, CA (US)

(72) Inventors: Ryan Boucher, San Francisco, CA (US); Lionel Nelson, Los Altos Hills, CA (US)

(73) Assignee: Zipline Health, Inc, San Francisco, CA (US)

( * ) Notice: Subject to any disclaimer, the term of this patent is extended or adjusted under 35 U.S.C. 154(b) by 839 days.

(21) Appl. No.: 17/319,042

(22) Filed: May 12, 2021

(65) Prior Publication Data

US 2021/0353230 A1    Nov. 18, 2021

Related U.S. Application Data

(60) Provisional application No. 63/023,769, filed on May 12, 2020.

(51) Int. Cl.
*A61B 5/00* (2006.01)
*A61B 1/00* (2006.01)
(Continued)

(52) U.S. Cl.
CPC ........ *A61B 5/6817* (2013.01); *A61B 1/00016* (2013.01); *A61B 1/227* (2013.01); *H04N 23/56* (2023.01); *H04N 23/555* (2023.01)

(58) Field of Classification Search
CPC ... A61B 5/6817; A61B 1/00016; A61B 1/227; H04N 23/56; H04N 23/555
See application file for complete search history.

(56) References Cited

U.S. PATENT DOCUMENTS 3,840,004 A * 10/1974 Heine .................... A61B 1/227
                                                            600/200
4,622,975 A * 11/1986 Danby ................ A61B 5/6817
                                                            600/379
(Continued)

FOREIGN PATENT DOCUMENTS

DE     20 2010 006026 U1    3/2011
EP           1903931 A1     4/2008
(Continued)

OTHER PUBLICATIONS

PCT International Search Report and Written Opinion, PCT Application No. PCT/US2021/032096, Sep. 2, 2021, 12 pages.

*Primary Examiner* — Nicholas J Plionis
(74) *Attorney, Agent, or Firm* — Foley Hoag LLP; John D. Lanza

(57) ABSTRACT

A diagnostic device is configured to capture diagnostic information about a subject (e.g., the subject's ears). The diagnostic device may include a diagnostic extension housing diagnostic elements (e.g., imaging chip, light sources, or lenses) and an ear canal engagement section coupled to the diagnostic extension. The ear canal engagement section may be shaped to position the diagnostic extension superiorly within the ear canal. For example, one side of the ear canal engagement section may be longer than another, which may enable the ear canal engagement section to contact the inferior wall of the ear canal for a longer distance than it contacts the superior wall. This configuration may allow more movement of the diagnostic extension when the device is inserted into the ear, which further improves the alignment of diagnostic elements with a desired area of the ear for diagnoses (e.g., the eardrum).

19 Claims, 22 Drawing Sheets

(51) Int. Cl.
    *A61B 1/227*     (2006.01)
    *H04N 23/56*     (2023.01)
    *H04N 23/50*     (2023.01)

(56) References Cited

U.S. PATENT DOCUMENTS

| | | |
|---|---|---|
| 11,011,271 B2 | 5/2021 | Boucher et al. |
| 2007/0261494 A1 | 11/2007 | Fuller et al. |
| 2014/0272221 A1 | 9/2014 | Forsyth et al. |
| 2016/0029974 A1* | 2/2016 | Armstrong ............ A61B 5/4815 600/479 |
| 2018/0353073 A1* | 12/2018 | Boucher .................. A61B 5/05 |
| 2020/0078509 A1 | 3/2020 | Bryning et al. |

FOREIGN PATENT DOCUMENTS

| | | |
|---|---|---|
| JP | 2004-041656 A | 2/2004 |
| WO | WO 2007/004083 A1 | 1/2007 |

\* cited by examiner

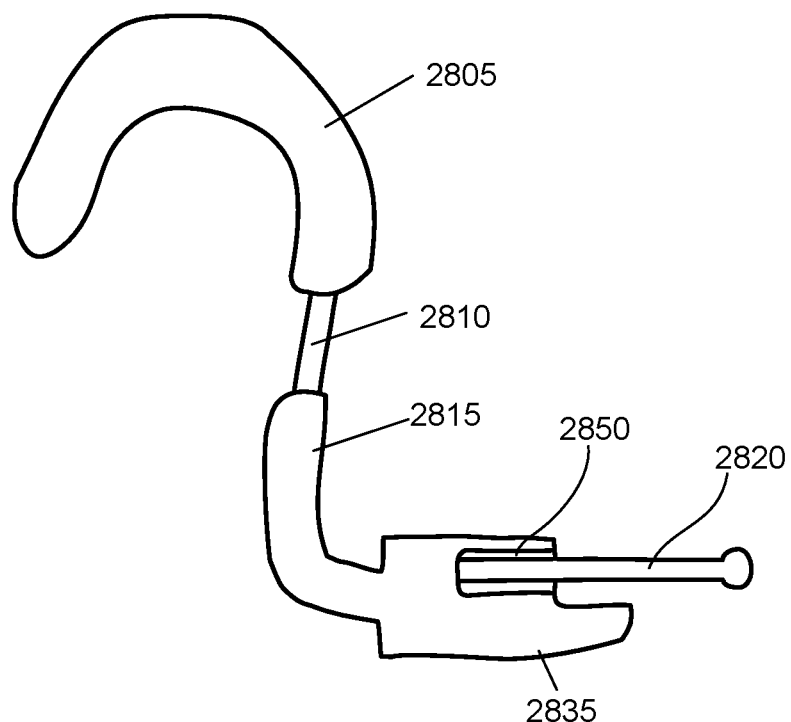
FIG. 28
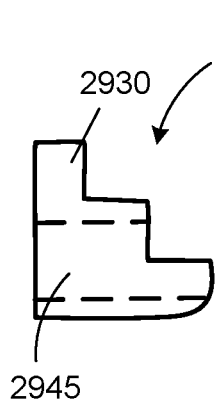
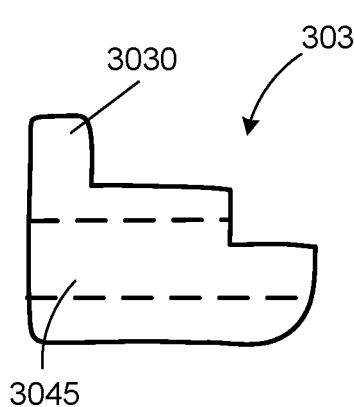
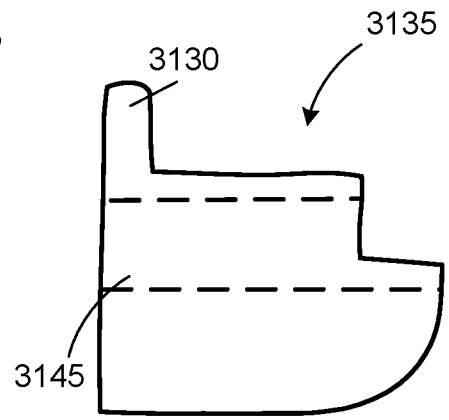
FIG. 29  FIG. 30  FIG. 31

DEVICES FOR AT-HOME PHYSICAL EXAMINATION OF THE EAR AND EAR CANAL

CROSS REFERENCE TO RELATED APPLICATIONS

This application claims the benefit of U.S. Provisional Application No. 63/023,769, filed May 12, 2020, which is incorporated by reference in its entirety.

TECHNICAL FIELD

The present disclosure relates to diagnostic devices for acquiring medical diagnostic information and, in particular, to diagnostic devices that enable patients to capture the information without the physical presence of a medical professional (e.g., for telehealth).

BACKGROUND

Medical diagnoses are typically performed by health care professionals at medical treatment centers. If the subject is a small child, or if the condition is thought to be serious or in need of immediate treatment, the long waiting periods for a physician appointment may seem unreasonable or unacceptable. The subject often goes to an emergency room or urgent care center on a "walk-in" basis, which often have long waiting periods. In some cases, the subject's visit may have been unnecessary, as the condition was not truly "urgent" or "critical," and thus treatment could have been delayed or accommodated at a regularly scheduled appointment, or the condition would have resolved itself with little or no intervention by the physician. Thus, a diagnostic device that is easily and safely handled without a physician is advantage to gauge whether a condition requires immediate intervention and/or treatment.

Conventional diagnostic devices for diagnosing a human subject's ears are difficult to align without professional help. For example, ear speculums are difficult to align within the canal and, additionally, the eardrum. These conventional diagnostic devices do not engage with a sufficient length of canal engagement that would otherwise secure positioning of the device to help non-professional align the device within the ear. Further, conventional diagnostic devices fail to achieve superior positioning or a superior angle of a flexible diagnostic extension for capturing diagnostic information at an extended depth of the ear canal (e.g., capturing information regarding the eardrum), when the ear is in a natural or neutral anatomical position (e.g., not pulled back to straighten the canal). Conventional devices also require the ear to be pulled to straighten the ear canal in order to insert an extension or ear speculum and image the eardrum. Conventional diagnostic devices may also fail to accommodate for the generally oval shape of the ear canal; thus, conventional diagnostic devices have a poor fit within the ear canal.

An ear may generally have limited space below, or inferior to, the entrance of the ear canal. Further, the intratragal notch is not aligned with the ear canal and it is a narrow space. This leaves little room inferiorly (i.e., there is a small target region of inferior space). There may be limited to no room anteriorly where the tragus extends in line with the anterior wall of the ear canal. Conventional diagnostic devices may have a stop configured to contact this inferior region or anterior, but these stops often come into contact with the tragus or anti tragus due to the narrow space. This contact may cause undesired movement of conventional diagnostic devices after a subject has obtained a desired position. Thus, conventional diagnostic devices are challenged to prevent over insertion (e.g., via a stop) while avoiding undesired forces from anatomy of the outer visible ear.

SUMMARY

Diagnostic devices and attachments are described herein for obtaining diagnostic information about a human subject (e.g., of the subject's ear). The diagnostic devices may include ear canal engagements that contact a wall of the ear canal at a sufficient length to secure or facilitate positioning or stabilization of the device. The diagnostic devices achieve superior positioning or angle of a diagnostic extension within the ear canal (e.g., when the ear is in a neutral or natural state). Cross sections of ear canal engagement sections of the diagnostic devices may be oval shaped to engage with the ear canal, which has a substantially oval-shaped cross section. Further, oval shape may provide desired positioning of the diagnostic extension and limit movement of the device when inserted into the ear canal due to the increased contact with ear canal walls. In some embodiments, ear canal engagement section is configured to contact the inferior wall of the ear canal for a longer length than it is configured to contact the superior wall of the ear canal. This relatively short, superior engagement may maintain a desired superior positioning, optionally together with a longer, inferior (i.e., downward or lower) engagement of a diagnostic extension, may stabilize the device, and allow more movement of the diagnostic extension within the ear canal. This movement may further assist a user in aligning the diagnostic extension with a region (e.g., the eardrum) where diagnostic information is captured. Diagnostic devices described herein may be structured with a superior stop, which may be no wider than the ear canal. In this way, the diagnostic device may prevent over insertion of a diagnostic extension within the ear canal while avoiding undesired forces from contact with anatomy of the visible outer ear (e.g., the anti tragus or tragus). In some embodiments, the diagnostic devices herein are used to capture diagnostic information about the mouth or throat in addition or alternatively to capturing diagnostic information about the ear.

A diagnostic device for obtaining diagnostic information about a human subject is described herein. The device may have an ear canal engagement section, a body, and a diagnostic extension. The ear canal engagement section may be coupled to the body and may include an insertion portion and a stop. The insertion portion may be configured to be inserted into an ear canal of the human subject. The insertion portion may have an upper portion and a sled that extends farther into the ear canal than the upper portion. The stop may extend from a top of the ear canal engagement section. The diagnostic extension may protrude from the insertion portion and be configured to extend into the ear canal. The diagnostic extension may have one or more diagnostic elements for obtaining the diagnostic information.

In some embodiments, the sled curves such that a distal end of sled points towards a superior wall of the ear canal when the sled contacts the inferior wall of the ear canal. The sled may be adapted such that the ear canal engagement section angles upward when the sled contacts an inferior wall of the ear canal. The diagnostic device may further include a first and a second portion of the body. The second portion of the body may include a cavity where a post may be configured to couple. The post may be configured to couple to an over ear piece. A second end of the post may be adapted to couple to the over ear piece. A first end of the over ear piece may include a cavity configured to receive the second end of the post. The surface of the cavity may be composed of a flexible material configured to expand around and compress onto the second end of the post. The first portion of the body and the second portion of the body may be coupled to one another at a flexible joint, wherein the flexible joint enables a first orientation of the body and a second orientation of the body. In the first orientation of the body, the first portion of the body may be orthogonal to the second portion of the body. In the second orientation of the body, the first portion of the body may be in line with the second portion of the body. The height of the stop may be approximately 25%-50% of the height of the ear canal engagement section. The stop may be flexible. The width of the stop may be no greater than the width of the ear canal engagement section.

The ear canal engagement section may include a tapered surface such that the height of the body is largest at the proximal end of the body. The ear canal engagement section may include a stepped surface such that the height of the body decreases in discrete steps, where the height of the body is largest at the proximal end of the body. The insertion portion may further include a channel through which the diagnostic extension extends from the insertion portion, where a height or width of the channel is greater than a height or width of the diagnostic extension, respectively. The height of the ear canal engagement section may be 5-13 millimeters. The diagnostic device may further include communications circuitry to wirelessly communicate the obtained diagnostic information to an external computing device. The diagnostic extension may have a curved shape and be composed of at least a rigid material to maintain the curved shape. The body may further include an air injection button and an air outlet port configured to pressurize the ear canal. The stop may be configured to conform to the subject's ear outside of the ear canal to seal the ear canal. The tip of the diagnostic extension (e.g., a bulb) may house a plurality of light sources and an imaging chip. The diagnostic extension may further include a spring.

BRIEF DESCRIPTION OF THE DRAWINGS

The disclosure will be understood more fully from the detailed description given below and from the accompanying figures of embodiments of the disclosure. The figures are used to provide knowledge and understanding of embodiments of the disclosure and do not limit the scope of the disclosure to these specific embodiments. Furthermore, the figures are not necessarily drawn to scale.

FIG. 28 depicts a device with a body connected to an over ear piece via a post, in accordance with at least one embodiment.

FIGS. 29-31 depict various attachments that fit onto the device of FIG. 28, in accordance with at least one embodiment.

DETAILED DESCRIPTION

Figure 1:
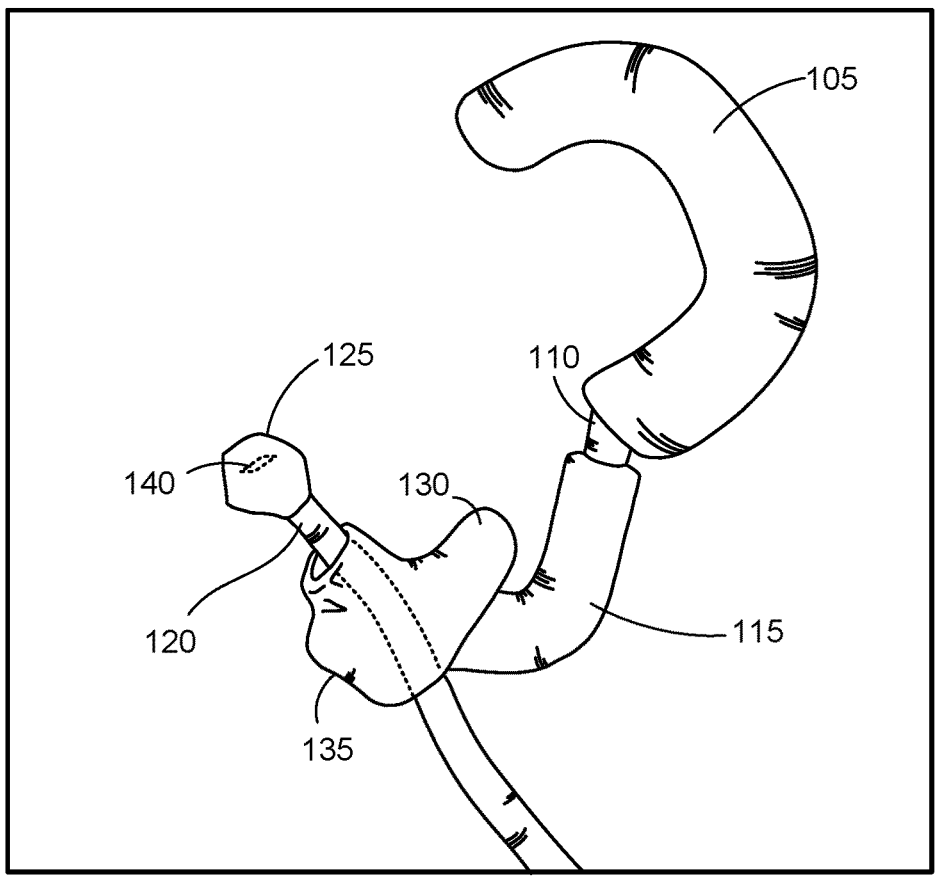
FIG. 1 depicts a diagnostic device for obtaining physiologic or medical diagnostic data in or near the ear canal, in accordance with at least one embodiment.

Aspects of the present disclosure relate to devices for at-home physical examination of the ear and the ear canal. The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Unless otherwise specified or apparent from the figures and the description, the following directions align with each other: height is equivalent to vertical and these generally align with an inferior-superior anatomical direction with the device in place in relation to the ear and anatomy. Likewise, width and horizontal are equivalent in the descriptions and generally align with an anterior-posterior anatomical direction with the device in place in relation to the ear and anatomy. Up aligns with superior, down with inferior, back with posterior, and front with anterior.

This description is broken down into different device parts and components. Any of these features and parts or components can be combined into a device, depending on the specific product desired. Various configurations of these features can produce a user friendly diagnostic device that can be positioned, stabilized, supported and aligned to enable people who are not health care professionals to capture diagnostic information.

In various embodiments, the diagnostic extension of the devices contains diagnostic elements that are positioned at or near its tip. The diagnostic elements may emit light and capture light. This light may be in the visible spectrum or in another spectrum, for example infrared light. Visible light helps visualize for redness or other signs of infection as well as fluid behind the eardrum and other pathologies. Infrared light may help analyze and diagnose across and behind the eardrum or capture infrared light emitted from the eardrum or ear canal walls to record temperature. Elements can also sense pressure or sound and be outlets for sound or air. Diagnostic elements may also be located on or in other parts of the device. For example, blood pressure sensors or pulse sensors or oxygen sensors may be located on an ear canal engagement section and be positioned on the device so that when the device is inserted and placed in the ear, these diagnostic elements are just inside the canal entrance.

In various embodiments, features described with respect to a particular figure may be implemented in other configurations. If the ear is pulled back and up to straighten the canal, as is often done when examining the ears, but not necessarily required with the configurations of devices described herein, the positioning features may move with the anatomy and maintain a generally desirable position of the diagnostic extension or diagnostic elements to capture diagnostic information.

Diagnostic extensions can take any of a variety of shapes and forms and characteristics. Rigid or flexible, straight or curved, small or large diameter. Diagnostic extensions are pictured with a generally smaller diameter and then a larger diameter or profile, such as a bulb, near the tip. The ear diagnostic extension in alternative embodiments is shaped more similar to a standard ear speculum, and more desirable a smaller cone than a standard ear speculum. A standard shaped ear speculum can also be configured with a larger diameter section at or near the tip, in various embodiments having a bulb shape and a soft material.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Example Devices and Attachments

FIG. 1 depict devices for obtaining physiologic or medical diagnostic data in or near the ear canal, in accordance with at least one embodiment. The device depicted in FIG. 1 includes over ear piece 105, post 110, body 115, diagnostic extension 120, bulb 125, stop 130, ear canal engagement section 135, and diagnostic element 140. The cross section of a device us depicted in FIG. 2, where the device includes over ear piece 205, post 210, body 215, diagnostic extension 220, bulb 225, and ear canal engagement section 235. Although not depicted, the devices may contain additional components such as an audio source (e.g., speaker) or audio receiver (e.g., microphone). The devices may be configured to capture images of the ear canal and ear dream. For example, one or more of the anatomical interfaces of the devices contact the walls of a user's ear canal to position a diagnostic extension of the device within the ear canal to capture images within the ear, where the diagnostic elements include a light source and a light capturing element, such as a lens and CMOS video chip. As referred to herein, an "anatomical interface" is a portion of a device that contacts anatomy to position, align, stabilize, or support the device or parts of the device, where the device captures a user's diagnostic information. Examples of anatomical interfaces may include over ear piece 105, diagnostic extension 120, stop 130, and ear canal engagement section 135. Main body 115 may include anatomical interfaces or different parts of one anatomical interface. For example, main body 115 in FIG. 1 is depicted as including stop 130 and ear canal engagement section 135.

Figure 3:
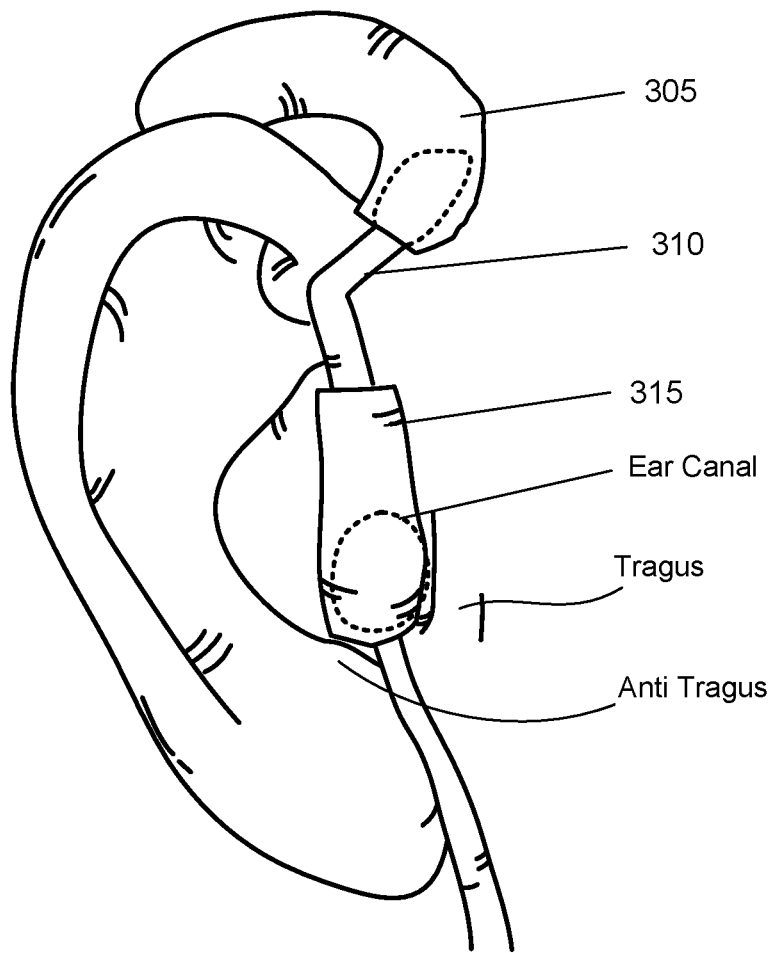
FIG. 3 depicts a diagnostic device in place on a user, in accordance with at least one embodiment.

Ear canal engagement section 135 is shaped to fit into a user's ear canal. In some embodiments, ear canal engagement section 135 is cylindrical or cuboid in shape. Stop 130 is configured to contact tissue of the outer visible ear near the canal. For example, stop 130 protrudes from the surface the device (e.g., from body 115) such that radius or profile of body 115 is greater than the height of the ear canal. This height may vary depending on ear size but in one example, may be greater than 10 millimeters. In some embodiments, over ear piece 105 wraps around the helix of a user's ear. An example of this is shown in FIG. 3. Diagnostic extension 120 may be flexible, allowing it to conform to the ear canal. Diagnostic extension 120 may be a tube, where one or more wires is located within the tube and connects to a diagnostic element (e.g., a camera) at the tip of diagnostic extension 120. In some embodiments, diagnostic extension 120 includes a spring to maintain the shape of diagnostic extension 120 when forces are absent that flex diagnostic extension 120 into a particular position (e.g., an opposing force applied upon contacting a wall of the ear canal that causes the diagnostic extension to bend). Diagnostic extension 120 may be composed of a material such as silicon, a lower durometer urethane, any suitable, flexible material, or a combination thereof. In some embodiments, at least some portions of diagnostic extension 120 may be composed of a rigid material.

In some embodiments, diagnostic extension 120 floats within a section (e.g., ear canal engagement section 135) of the device. That is, motion of the diagnostic extension may be independent of the motion of the section of the device. For example, diagnostic extension 120 may be extended into the ear canal by a distance without requiring the section to extend into the ear canal by the same distance. Further, by floating within a section of the device, diagnostic extension 120 may move further in the ear canal with less bending than when diagnostic extension 120 is restricted and not floating. For the example, diagnostic extension 120 may move up/down, side/side and/or become angled under force from the ear canal walls prior to forces causing bending. In one example, diagnostic extension 120 is restricted and not floating when it is connected to ear canal engagement section 135 at an opening of section 135 (e.g., the opening within the ear canal when the device is in place on the user). In some embodiments, the end of diagnostic extension 120 includes bulb 125. That is, the distal end of diagnostic extension 120 may be shaped similar to a bulb, sphere, or cylinder having a larger diameter than the proximal section of diagnostic extension 120. In some embodiments, the distal end may have a different shape that has a larger diameter or profile than the more proximal section of diagnostic extension 120. The terms "profile" and "cross section" may be used interchangeably herein unless specified otherwise by context.

Figure 2:
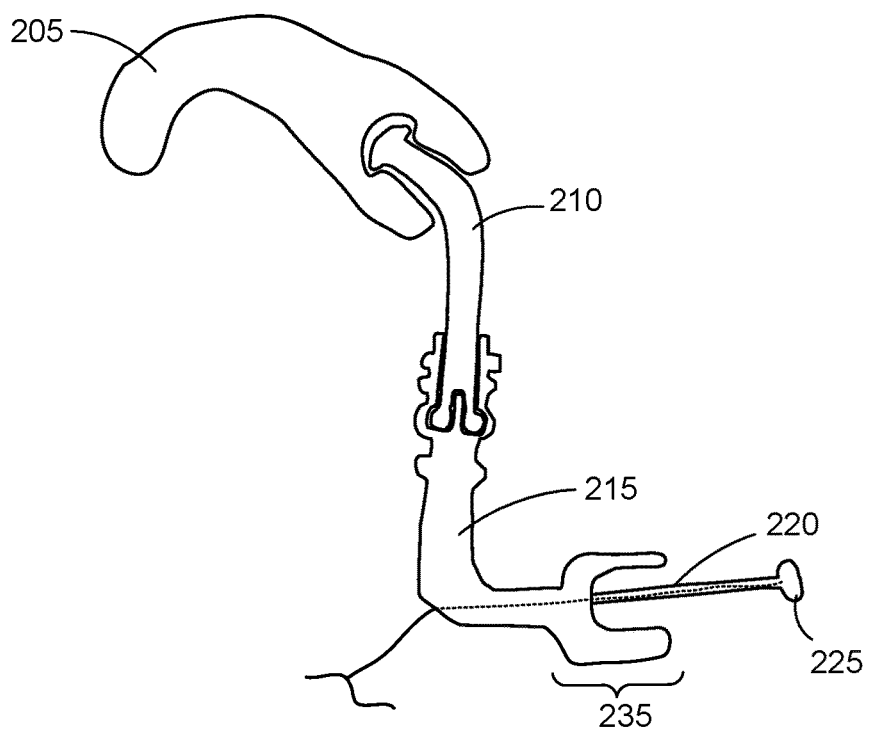
FIG. 2 depicts a cross section of a diagnostic device, in accordance with at least one embodiment.

The devices in FIGS. 1 and 2 are shown with wires coupled to the devices. For example, the wires may be connected to bulb 125 at one end and connected to an external device or power source. An external device may be a computing device such as a smartphone or desktop computer. In some embodiments, the external device may generate audio that may be communicated to the device via stereo audio cables. The wires may channel one or more of power, light, audio, or data to or from the devices. The wires may include communications or networking cables such as fiber optic cables, twisted pair cables, or any suitable cable for communicating diagnostic information captured by the device (e.g., images of the ear canal). The wires may include a power cord coupling the device to a power source such as a battery. The wires may also include cables for transmitting light to illuminate areas of the body for capturing diagnostic information (e.g., images or videos of the ear canal or throat). Such cables may be composed of any suitable material for transmitting light without significant loss over a short distance (e.g., within a half a meter).

In some embodiments, the device may be coupled via wires or wirelessly to an external box that is designed to communicate with the device. For example, the external box may contain a battery, one or more processors, and communications circuitry (e.g., WiFi or Bluetooth chip). In some embodiments, the external box may be further connected to a computing device such as a smartphone or desktop computer. In some embodiments, a device may be wireless (i.e., no wires are coupled to the device). The device may contain components such as a battery, communications circuitry, or processors that may otherwise be externally connected via wires. In some embodiments, the device may have a data input/output port to receive a cable to couple the device to an external computing device such as a computer or smartphone. The input/output port may include a universal serial bus (USB) type port, external serial advanced technology attachment (eSATA) port, or any suitable port having a form factor suitable for mobile health diagnostic devices.

A cross section of a device is depicted in FIG. 2. The device shown in FIG. 2 may be a variation of the device shown in FIG. 1. Diagnostic extension 220 may float within ear canal engagement section 235. A wire may connect diagnostic extension 220 to body 215. That is, diagnostic extension 220 may move independently of ear canal engagement section 235 but may be fixed or unremovable from the device due to the wire preventing diagnostic extension 220 from fully separating from body 215 of the device. Diagnostic extension 220 may be connected by a variety of means such as by adhesive or clamping. Body 215 of the device may be a curved structure (e.g., J-shaped) with two ends, where a first end has an opening from which one or more of a wire or diagnostic extension 220 may exit and a second end having an opening, which may also be referred to herein as a "cavity," to receive post 210. The second end configured to receive post 210 may be a tube whose inner surface is concave with one or more grooves corresponding to various positions at which post 210 may fit into body 215. In some embodiments, body 215 has grooves configured as a ring around the inner surface of body 215.

Post 210 of the device may be a hollow or solid tube having two ends, where a compressible, slotted ring is located at one end and a rigid or compressible sphere or bulb is located at the other. Alternative shapes and cross sections may be used instead of a sphere or bulb, such that the end is configured to mate with an opening or cavity in one end of over ear piece 205. The ring of post 210 may compress through narrower diameter portions of the cavity of body 215, the cavity that is configured to receive post 210, and expand upon contact with grooves within the inner surface of the cavity. The depth of the grooves of body 215 or the diameter of the slotted ring of post 210 may be such that post 210 is securely coupled to body 215 when no user force is applied (e.g., the user's force applied to extract post 210 from the cavity of body 215). The grooves and rings of post 210 and body 215 enable the two components of the diagnostic device to attach to one another and rotate relative to one another, for example to rotate the over ear piece in order to use the device in the left or right ear. That is, body 215 can rotate about post 210 in the same plane in which the rings reside. The position of post 210 within the cavity of body 215 configured to receive post 210 may be adjustable via grooves within the inner surface of body 215 at various positions along the cavity. For example, a first position for post 210 to be located at may be one millimeter from the cavity's entrance, a second position may be 3 millimeters from the entrance, and a third position may be 5 millimeters from the entrance. The ring of post 210 may snap into a desired ring of body 215.

The size of over ear piece 205 may vary to fit different sizes of ears. For example, a diagnostic kit may include post 210, body 215, and varying sizes of over ear piece 5. In some embodiments, over ear piece 205 is a hollow or solid tube, where a first end of the tube includes a cavity to enable post 210 to couple to over ear piece 205. For example, the cavity may be a spherical cavity to allow a bulb at one end of post 210 to fit within the spherical cavity. The bulb of post 210 may be compressible to fit into the cavity of over ear piece 205 or the material of over ear piece 5 may be expandable to receive post 210. Over ear piece 205 may have a curved shape (e.g., C-shaped) to fit over the helix of an ear. Over ear piece 205 may include a flexible material (e.g., silicon). Alternatively, a variety of sizes of over ear pieces and posts that are permanently connected may be included in a diagnostic kit.

While a wire is shown exiting the device of FIG. 2, in some embodiments, one or more wires may be located within the device (e.g. within the tube structures of body 215, post 210, over ear piece 205, etc.). For example, a wire may travel from diagnostic extension 220, where it receives diagnostic data (e.g., captured by a camera at diagnostic extension 220), through body 215, then through post 210, and into over ear piece 205. In some embodiments, over ear piece 205 includes a hollow area sized to contain one or more of a processor, light source (e.g., light emitting diode (LED)), speaker, or communications circuitry. Over ear piece 205 may be attached to post 210 in a fixed manner (e.g., there is no snapping mechanism with an cavity for post 210 to be coupled and decoupled by a user from over ear piece 205). For example, where over ear piece 205 includes a hollow area sized to contain electronics such as a processor or communications circuitry, over ear piece 205 may be fixed to post 210. Over ear piece 205 may be flexible and elastic to adjust to different sizes of ears. A C-shape of over ear piece 205 may be made of a moldable material or contain a moldable material. In some embodiments, a moldable over ear piece 205 may be formed (e.g., shaped by a user) to fit an ear or over ear piece 205 may stretch to fit over the helix of a larger ear or compress to fit over the helix of a smaller ear.

FIG. 3 depicts a diagnostic device in place on a user, in accordance with at least one embodiment. The device may be similar to the devices shown in FIGS. 1-2. The device includes over ear piece 305, post 310, and body 315. Over ear piece 305 may be located around the helix of the ear and help to support, position, or stabilize the device. In the example configuration of FIG. 3, post 310 has a grooved external ring (i.e., a ring protruding from the external surface of post 310) that may compress and expand due to a flexible material from which post 310 or at least the slotted ring is made. There may be internal rings (i.e., a ring caving into the inner surface of body 315) in body 315 of the device to fit the external ring of post 310. The rings enable post 310 to be raised or lowered and secured at different positions.

Ear canal engagement section is located inside the ear canal and behind (i.e., obscured from view by) body 315 within the view presented in FIG. 3. The ear canal is depicted behind body 315 via dashed lines. Although obscured from the view shown in FIG. 3 by body 315 of the device, a stop may be attached to body 315 and may remain outside the canal in this configuration. In some embodiments, the stop may partially enter the canal or even fully enter the canal. For example, the stop may be a protrusion located on the surface of an ear canal engagement section that has a height of 25% of the maximum height of the ear canal engagement section. In another example, the stop may have a height of 5% of the maximum height of the ear canal engagement section, which may enable the stop to be inserted into the ear canal only a short distance (e.g., less than 5 millimeters into the canal). In some embodiments, the stop can be inserted to until a certain point inside the canal, which changes shape and decreases in diameter as it approaches the isthmus of the canal. In some embodiments, the stop is at least larger in size than the isthmus of the canal. In one example, the ear canal engagement size is sufficient to also serve as the stop without an additional protrusion. In another example, the stop protrudes between 1 to 3 millimeters away from the surface of the ear canal engagement section. In another example, the stop may be located at one point on the ear canal engagement section. For example, the stop may be located at one end of the ear canal engagement section opposite the end configured to enter the ear canal first. A stop may be located on one side of the ear canal engagement section, for example on the upper or superior side, such that a user may position the device for the stop to contact the helix crus or helicis crus, which is located superiorly, or above, the canal. Since the concha cavum is located medially to the helix crus, and the posterior wall of the canal starts at this medial point, the ear canal engagement section in this configuration may extend a distance from the helix crus to the where the posterior wall of the wall begins. This distance varies with person, ear size and age. For example, the distance may be approximately 1-2 millimeters for younger people or smaller ear anatomy, it may be 5 millimeters or more in certain people depending on variations of anatomy, or be this size or larger in older people. It is desirable then that the ear canal engagement section extends a longer distance from stop 30 than the anatomical distance from the helix crus to the beginning of the posterior wall of the canal to ensure this anatomical interface section fully engages with the ear canal. For example, the ear canal engagement section may be a length between 4-10 millimeters.

The width of the ear canal engagement section may be narrower at the distal end (i.e., the end of the device inserted into the ear) than the body 315 proximal to the ear canal engagement. In some embodiments, the width of body 315 angles out wider, equally on both sides, as it extends out laterally (more device proximal) from the ear canal engagement. This way, the width of body 315 may be symmetrical. In another example, the width of a proximal segment of body 315 may be narrower than the ear canal section. For example, the width may be 3 millimeters. In some embodiments, the width of body 315 is equal to or less than the width of the ear canal engagement section, which may help limit interference with the tragus.

In some embodiments, the width of a proximal segment of body 315 may be wider than the ear canal engagement section, which enables contact with the tragus to stabilize the device against the tragus. In such embodiments, the width of the ear canal engagement section may be substantially the same width as the ear canal. For example, the width of ear canal engagement section may be from 5 to 10 millimeters. This may help maintain body 315 in a particular position regardless of forces of the tragus on body 315 of the device.

In some embodiments, the inferior part of body 315 is equal to, or more superior to, the inferior part of the ear canal engagement section. One example is depicted in FIGS. 1-2 where an ear canal engagement section is at a lower location on the upright devices than the rest of the body. This structuring may limit interference on the device from the antitragus while the device is being inserted or while aligning the extension with the ear canal or eardrum when the ear is pulled back and up to straighten the ear canal. In some embodiments, the inferior part of body 315 is more inferior than the ear canal engagement section. This structuring may enable body 315 to be located in the concha behind the antitragus or enable body 315 to contact the antitragus to stabilize the device against the antitragus. When the inferior part of body 315 is more inferior than the ear canal engagement section, the width of the ear canal engagement section may be substantially the width of the ear canal to limit motion of ear canal engagement section due to the forces of the concha or antitragus on the device. Thus, the device's structure helps maintain a desirable position for capturing diagnostic information.

Figure 4:
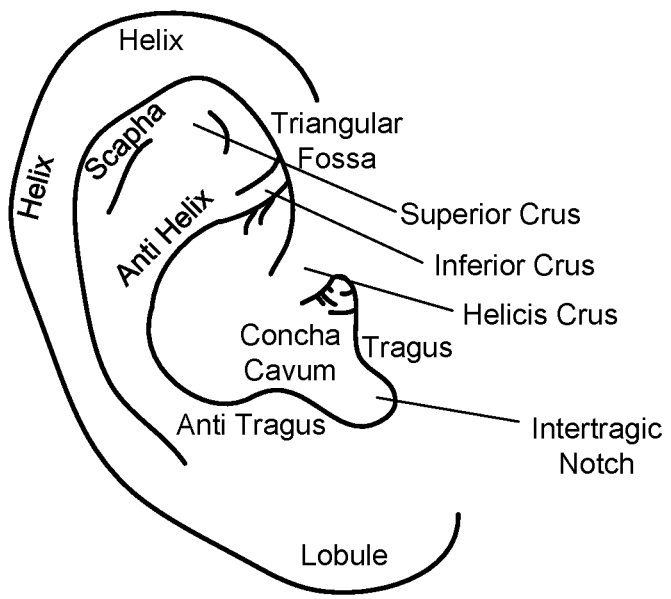
FIG. 4 depicts the outer visible ear anatomy.

In some embodiments, the inferior part of the device aligns with the intertragic notch. For example, the inferior part of the device may be structured with a width of 2-3 millimeters to fit within the width of the intertragic notch. The inferior part of the device may include a protrusion from the body 315. This protrusion may serve as a stop or stabilizer for the device. By aligning with the intertragic notch, the device may avoid interference from the ear's anatomy. A wire coupled to the device may also align with this intertragic notch, limiting interference with anatomy or providing stability by fitting into this location. For example, the wire may be structured to exit from body 315 at an opening on the surface of body 315 at the inferior part of the device such that the wire exits near the intertragic notch when the device is worn by a user. FIG. 4 depicts the outer visible ear anatomy, which includes the helix, scapha, anti helix, triangular fossa, concha cymba, concha cavum, superior crus, inferior crus, helicis crus, tragus, intertragic notch, anti tragus, and lobule.

Figure 5:
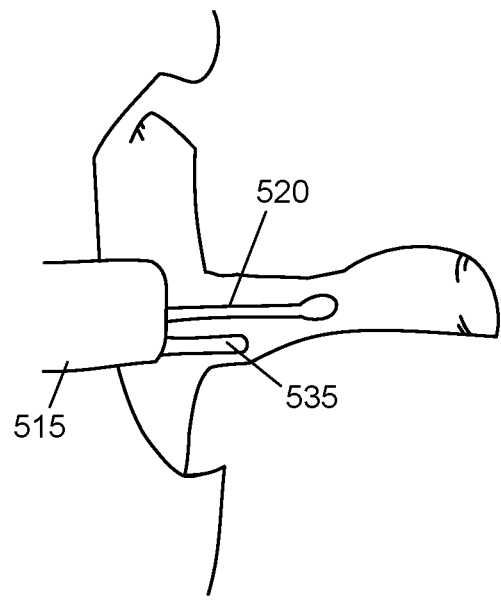
FIG. 5 depicts an ear canal engagement section of a device that is configured to contact at least one side of an ear canal wall, in accordance with at least one embodiment.

FIG. 5 depicts an ear canal engagement section of a device that is configured to contact at least one side of an ear canal wall, in accordance with at least one embodiment. Ear canal engagement section 535 contacts the inferior wall of the ear canal when the extension is inserted into the canal. For example, ear canal engagement section 535 includes a linear extension coupled to body 515. Diagnostic extension 520 may be coupled to body 515 (e.g., via a wire through body 515) and exit body 515 from the center of a segment (e.g., a cylindrical segment) of body 515. The linear extension of ear canal engagement section 35 may be connected away from the center of the segment and closer to the outer perimeter of the segment. The linear extension may be at a location closer to the inferior of body 515 such that ear canal engagement section 535 contacts the inferior wall of the ear canal.

The linear extension may be located at any location around the segment and extending in the same direction as the segment (i.e., such that the extension and segment of the body point towards the ear canal when the user is wearing the device). The linear extension may limit or prevent motion in corresponding directions. For example, the structure depicted in FIG. 5 may limit motion of the device or the diagnostic extension downward when it is inserted into the ear canal due to the contact of the linear extension of ear canal engagement section 535 with the inferior wall of the ear canal. In another example, ear canal engagement section 535 is structured to one horizontal side of extension that is intended to align inside the anterior wall of the ear canal, which provides some distance between diagnostic extension 520 and the anterior wall. This way, ear canal engagement section 535 maintains the position of diagnostic extension 520, which may include diagnostic elements such as a camera, within a particular position for capturing diagnostic information. Ear canal engagement section 535 may stabilize the position of diagnostic extension 520 or the device due to its contact against a wall of the ear canal while diagnostic data is captured. Ear canal engagement section 535 may enable the device to be pivoted or rotated with support against the canal wall, the canal engagement then contacting different segments of the canal wall.

Figure 6:
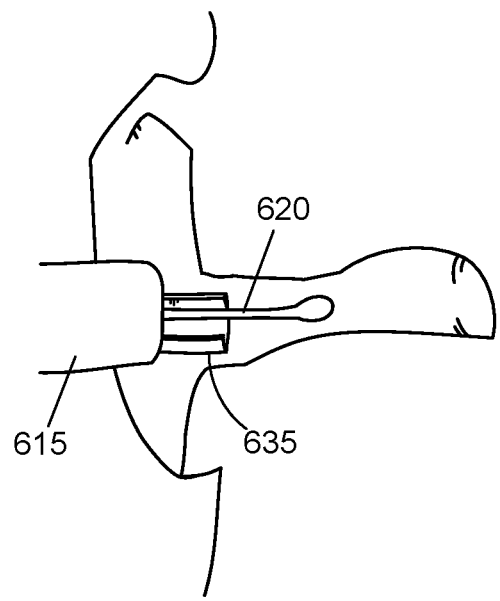
FIG. 6 depicts a semi-circle configuration of an ear canal engagement section that is configured to contact at least one side of an ear canal wall, in accordance with at least one embodiment.

FIG. 6 depicts an semi-circle configuration of an ear canal engagement section that is configured to contact at least one side of an ear canal wall, in accordance with at least one embodiment. For example, ear canal engagement section 635 may include a hollow semi-circle tube. Although described as having a semi-circle shape, ear canal engagement section 635 may include a tube having a perimeter less than the semi-circle's perimeter or greater than the semi-circle's perimeter (i.e., while having a perimeter that is greater than a linear extension's width or less than a full circle). The semi-circle tube may have a radius that is substantially equivalent to that of an ear canal or slightly less (e.g., between 2-5 millimeters), which enables ear canal engagement section to contact the ear canal walls. In the example shown in FIG. 6, the perimeter of ear canal engagement section 635 may simultaneously contact the inferior and posterior walls of the ear canal. Ear canal engagement section 635 may thus maintain distance between diagnostic extension 620 and the inferior and posterior walls of the ear canal. Ear canal engagement section 635 may contact any combination of anterior, superior, inferior, and posterior walls of the ear canal, which enables diagnostic extension 620 to maintain some distance between the corresponding contacted wall.

Figure 7:
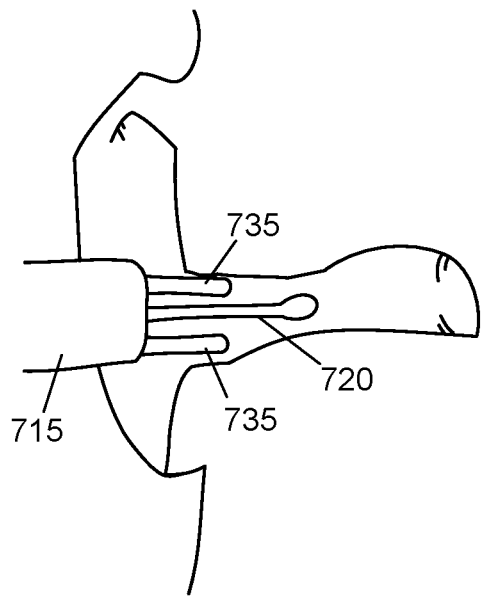
FIG. 7 depicts an ear canal engagement section that is configured to contact opposite sides of an ear canal wall, in accordance with at least one embodiment.

FIG. 7 depicts an ear canal engagement section that is configured to contact opposite sides of an ear canal wall, in accordance with at least one embodiment. Ear canal engagement section 735 may include two linear extensions coupled to body 715 such that the linear extensions are located opposite one another. For example, the two linear extensions may be coupled to cylindrical, or other shaped, segment of body 715 and extend in the direction of the segment (i.e., in the direction of the ear canal when the device is worn by a user). The two linear extensions may be located at opposite sides of the cylindrical segment. Although only two linear extensions are shown, ear canal engagement section 735 may include any suitable number of linear extensions. The extensions may be located in a circle and coupled to body 715. Ear canal engagement section 735 may limit motion of diagnostic extension 720 within the ear canal in the corresponding directions from diagnostic extension 720 to the linear extensions of ear canal engagement section 735.

Figure 8:
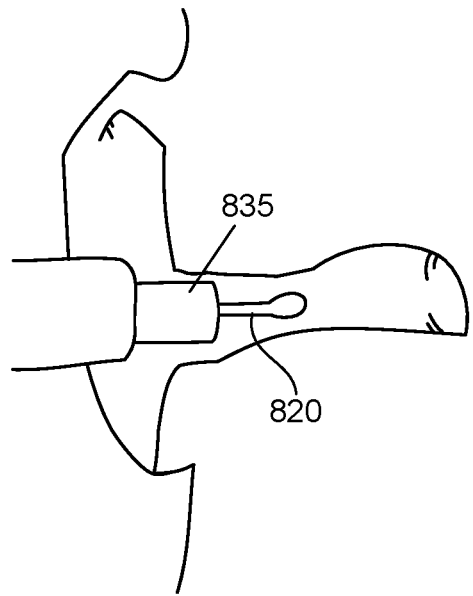
FIG. 8 depicts a circular ear canal engagement section that is configured to contact all canal walls, in accordance with at least one embodiment.

FIG. 8 depicts a circular ear canal engagement section that is configured to contact all canal walls, in accordance with at least one embodiment. Ear canal engagement section 835 may include a tube surrounding diagnostic extension 820. Ear canal engagement section 835 helps maintain distance between diagnostic extension 820 from all canal walls. The cross section of ear canal engagement section may be circular, oval, or any suitable shape to fit within the ear canal and maintain a distance between diagnostic extension 820 and the ear canal walls.

Figure 9:
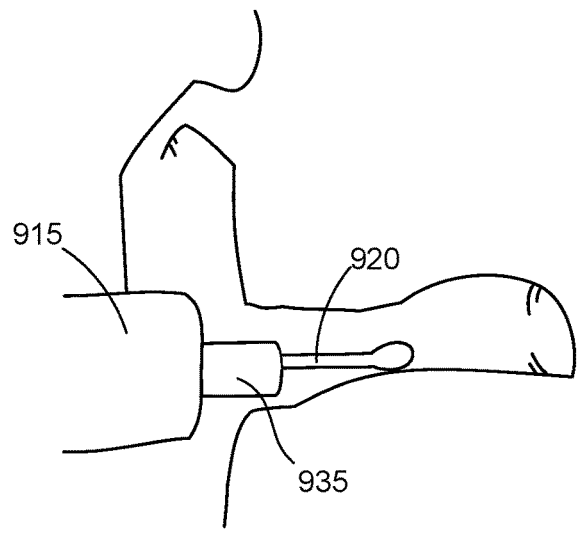
FIG. 9 depicts an ear canal engagement section that is undersized relative to an ear canal, in accordance with at least one embodiment.
Figure 10:
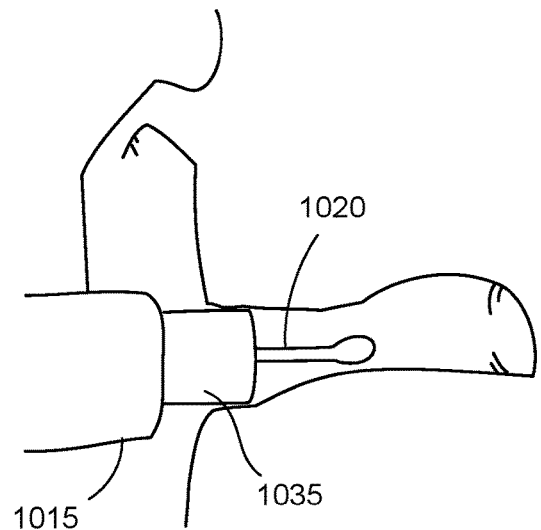
FIG. 10 depicts an engagement section that is closely shaped to the canal, in accordance with at least one embodiment.

FIG. 9 depicts an ear canal engagement section that is undersized relative to an ear canal, in accordance with at least one embodiment. Ear canal engagement section 935 is coupled to body 915 and houses diagnostic extension 920. In some embodiments, ear canal engagement section may be a cylindrical tube whose diameter is within a range of 4-9 millimeters such that it is undersized relative to an ear canal, which may have a diameter of 5-10 millimeters. The undersized structure may allow for a greater number of positions in which diagnostic extension 920 may rest within the ear canal than a structure that is sized closer to the ear canal size and which may contact all walls of the ear canal (e.g., as shown in FIG. 10). A user may manipulate and optimize the position of diagnostic extension 920 within some range prior to ear canal engagement section 35 contacting the ear canal walls and limiting further movement.

FIG. 10 depicts an engagement section that is closely shaped to the canal, in accordance with at least one embodiment. Ear canal engagement section 1035 is coupled to body 1015 and houses diagnostic extension 1020. Diagnostic extension 1020 may exit ear canal engagement section 1035 in a particular position relative to the canal with little additional motion or positioning allowed by the user.

Figure 11:
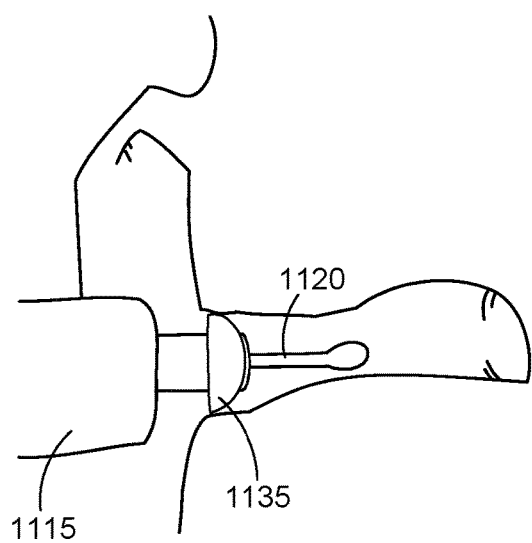
FIG. 11 depicts a flexible engagement section around an internal portion of the engagement section, in accordance with at least one embodiment.

FIG. 11 depicts a flexible engagement section around an internal portion of the engagement section, in accordance with at least one embodiment. Ear canal engagement section 1135 may be coupled to body 1115 and include a cylindrical tube and a flexible portion at the distal end of the cylindrical tube. The flexible portion may be a hollow semi-sphere in shape that is made of a flexible material such as silicon. The diameter of the flexible portion may be substantially equivalent to the width of the ear canal such that the flexible portion contacts all walls of the ear canal. This flexible portion may bend to conform to the shape of the ear canal walls and limit movement of diagnostic extension 1120 once the flexible portion is positioned into the ear canal. Due to the flexible material of the flexible portion, the flexible portion may conform to various positions as the canal shape and size changes as the device is advanced into the ear canal. The flexibility of the structure further helps ear canal engagement section 1135 fit different ear and anatomy sizes and shapes. Ear canal engagement section 1135 may serve as a seal to allow acoustic or pressure diagnostics. For example, a port distal to this flexible section can be connected to a pressurizing means in the device. The ear canal may be pressurized and the eardrum visualized for motion to help determine if there is fluid behind the eardrum. The internal part of ear canal engagement section 1135 or the outer flexible part of ear canal engagement section 1135 may serve as a stop as the device is inserted and the ear canal decreases in size. The internal size of ear canal engagement section 1135 may contact the internal walls of the canal and thus, limit or prevent movement of the device further into the ear canal.

Figure 12:
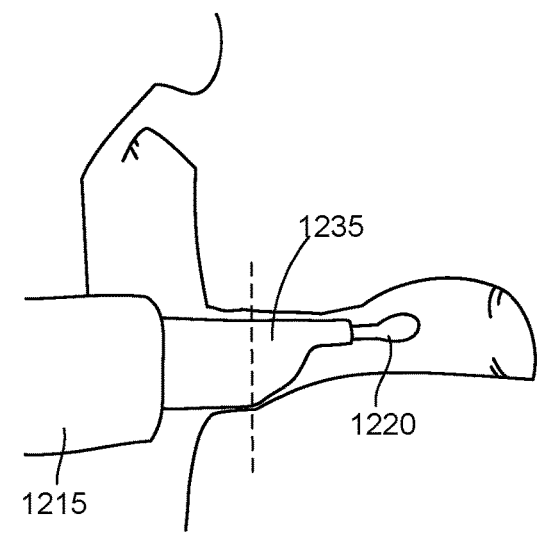
FIG. 12 depicts an ear canal engagement section that is part of the diagnostic extension, in accordance with at least one embodiment.

FIG. 12 depicts an ear canal engagement section that is part of the diagnostic extension, in accordance with at least one embodiment. Ear canal engagement section 1235 is coupled to body 1215 and houses diagnostic extension 1220. In some embodiments, ear canal engagement section 1235 is constructed using multiple materials, where a distal portion of ear canal engagement section 1235 is constructed to be more flexible than a proximal portion of ear canal engagement section 1235. For example, ear canal engagement section 1235 is a hollow shape composed of silicon with varying thickness around the dotted line as shown in FIG. 12. The thickness of the silicon may be largest at the portion of ear canal engagement section 1235 contacting body 1215 and decrease in thickness as the width of ear canal engagement section 1235 narrows towards the distal end of ear canal engagement section 1235, enabling the portion of ear canal engagement section 1235 to the right of the dotted line to be relatively more flexible than the portion of ear canal engagement section 1235 to the left of the dotted line. In some embodiments, ear canal engagement section 1235 has a geometry that changes over its length. For example, one side of ear canal engagement section may taper as shown in FIG. 12 (e.g., the section contacting the inferior wall of the ear canal once the device is worn by the user). In some embodiments, ear canal engagement section 1235 may also serve as a stop due to the width or height of ear canal engagement section 1235 being equal to or greater than the corresponding dimension (e.g., diameter) of the canal at some distance within the canal (e.g., at the dotted line). At this distance, the contact between ear canal engagement section 1235 and the ear canal walls may prevent the device from moving further into the ear canal.

Figure 13:
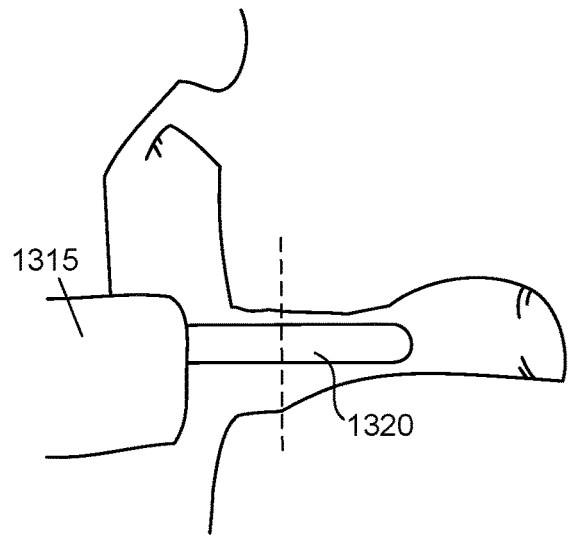
FIG. 13 depicts an extension that is flexible, in accordance with at least one embodiment.

FIG. 13 depicts an extension that is flexible, in accordance with at least one embodiment. In some embodiments, diagnostic extension 1320 is configured to vary in flexibility at different portions of diagnostic extension 1320. For example, diagnostic extension 1320 as shown in FIG. 13 may be more flexible to the right of the dotted line than the portion of diagnostic extension 1320 to the left of the dotted line. Diagnostic extension 1320 may be composed of a flexible material such as silicon. The length of diagnostic extension 1320 may include a tube where the thickness of the tube varies along the length. For example, the tube of diagnostic extension 1320 may be thickest at the location where diagnostic extension 1320 exits body 1315 and thinnest closest to the distal tip. This distal tip may be configured with a larger cross section than the more proximal segment of the diagnostic extension. For example, in a shape of a bulb, sphere, or cylinder with a larger diameter than the proximal segment of the extension. A portion of the tube having thinner thickness may be more flexible than a portion having thicker thickness. The less flexible (i.e., stiffer) portion of diagnostic extension 1320 may help diagnostic extension 1320 be positioned in the ear canal and prevent motion towards the canal walls. For example, diagnostic extension 1320 may stop or limit the device's movement within the ear canal upon contact with the ear canal rather than bending and allowing the device to continue moving within the ear canal. Diagnostic extension 1320 may include a portion that is flexible to conform to the canal shape. This flexible portion may align with the canal and be in a position to capture diagnostic data, such as images of the eardrum.

Figure 14:
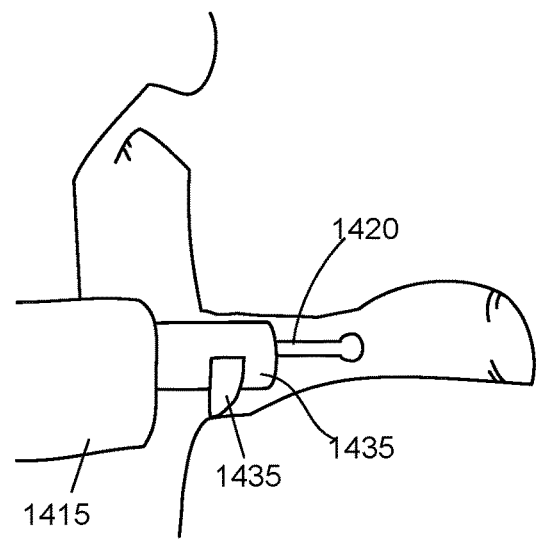
FIG. 14 depicts an ear canal engagement section that is flexible and includes a secondary engagement section to maintain a particular position of a primary engagement section, in accordance with at least one embodiment.

FIG. 14 depicts an ear canal engagement section, which may be flexible or rigid, that includes a secondary flexible engagement section to maintain a particular position of a primary engagement section, in accordance with at least one embodiment. In some embodiments, ear canal engagement section 1435 includes various sections, including a primary engagement section through which a wire coupled to diagnostic extension 1420 or through which diagnostic extension 1420 exits. The various sections may include a secondary engagement section that, like the primary engagement section, is configured to contact the user's ear canal. The primary engagement section may be a tube and the secondary engagement section may be a protrusion from the surface of the primary engagement section (e.g., the fin shape as shown in FIG. 14). One or more of the primary and secondary engagement sections may be flexible (e.g., made of silicon). The location of the secondary engagement section may be on a side of the primary engagement section such that secondary engagement section protrudes in a direction orthogonal to the direction of the primary engagement section configured to extend into the ear canal. For example, as shown in FIG. 14, the secondary engagement section is located at a lower or inferior part of ear canal engagement section 1435 to contact the inferior wall of the ear canal when the device is inserted in the user's ear. The secondary engagement section, although depicted at the lower part of ear canal engagement section 1435, may be located around the primary engagement section at any position. The position of the secondary engagement section enables a corresponding distance between the primary engagement section and the ear canal wall contacted by the secondary engagement section, which in turn, enables a particular position of diagnostic extension 1420 when the device is inserted into the user's ear. In this way, this flexible embodiment of ear canal engagement section 1435 can bend to accommodate smaller ears and is more extended in larger ears while providing force against the ear canal wall to achieve a particular position of diagnostic extension 1420 (e.g., a superior position as opposed to an inferior position). In some embodiments, ear canal engagement section 1435 includes the primary engagement section that is flexible and is coupled to diagnostic extension 1420 at a predetermined location at the end of ear canal engagement section 1435 (e.g., centrally, superior, inferior, anterior or posterior, etc.). In some embodiments, ear canal engagement section 1435 includes only the secondary engagement section that is flexible and coupled to diagnostic extension 1420 at a position along the length, for example 5 mm or 10 mm from the tip, and in a desired orientation (e.g. superiorly, inferiorly, posteriorly or anteriorly). In some embodiments, ear canal engagement section 1435 includes more than one secondary flexible engagement section coupled to diagnostic extension 1420 at a position along the length and in desired orientations.

Figure 15:
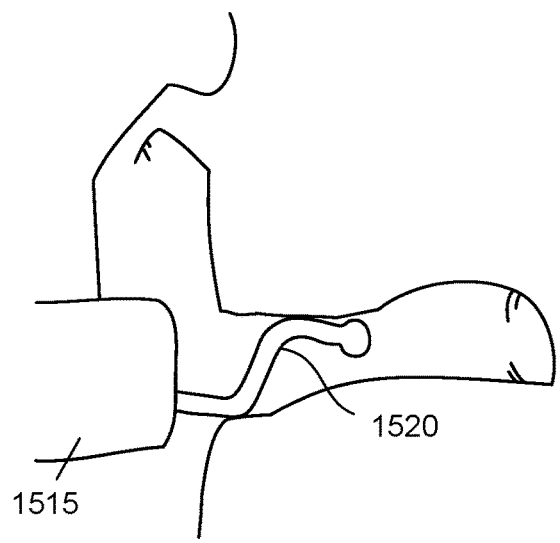
FIG. 15 depicts a diagnostic extension of a device, in accordance with at least one embodiment.

FIG. 15 depicts a diagnostic extension of a device, in accordance with at least one embodiment. In some embodiments, diagnostic extension 1520 may function similarly to an ear canal engagement section by contacting the ear canal at one or more locations to position diagnostic extension 1520 at a desired position. Diagnostic extension 1520 may be shaped such that at least one side is offset from the tip of diagnostic extension 1520 to maintain distance from the canal wall in the direction(s) of the at least one side. For example, diagnostic extension 1520 may have an S-shape where the tip of diagnostic extension 1520 is at one end of the shape at the other end is coupled to body 1515. As shown in FIG. 15, diagnostic extension 1520 is offset in two directions from the end of diagnostic extension 1520. This structure may create distance from two different sides of the canal wall and the tip of diagnostic extension 1520 and also limit rotation of the device and diagnostic extension 1520. This distance and limited rotation may help maintain a desired position of diagnostic extension 1520. Diagnostic extension 1520 may be a tube having any suitable number of bends in the tube (e.g., more than the two bends depicted in FIG. 15). Diagnostic extension 1520 may be constructed such that the distance between two successive bending locations is equal to or greater than distance from one point on an ear canal wall to a second point the opposite side of the ear canal (e.g., 12 millimeters). For example, diagnostic extension 1520 is constructed with a segment between two bending locations that is long enough to enable the two bending locations to simultaneously contact the ear canal wall when the device is inserted into the ear. In some embodiments, diagnostic extension 1520 may be constructed such that the distance between two successive bending location is shorter than the distance between two points on the ear canal walls. The size of the shape relative to the canal as well as the flexibility of diagnostic extension 1520 may determine how much the user is able to further change the position of diagnostic extension 1520. For example, a rigid configuration sized close to the canal size may significantly limit the amount of further positioning that a user can achieve, while a more flexible configuration sized smaller than the canal may allow significant additional motion while the device is being placed and after it is placed.

Figure 16:
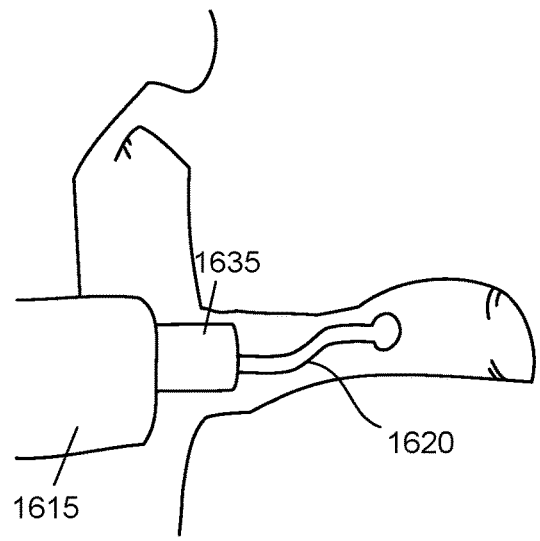
FIG. 16 depicts a diagnostic extension and ear canal engagement section of a device, in accordance with at least one embodiment.

FIG. 16 depicts a diagnostic extension and ear canal engagement section of a device, in accordance with at least one embodiment. In some embodiments, the device includes ear canal engagement section 1635 and diagnostic extension 1620, where diagnostic extension 1620 is curved similar to the configuration described in FIG. 15. This curved shape of diagnostic extension 1620 may enable diagnostic extension 1620 to possess functionality similar to that of ear canal engagement section 1635. The configuration of ear canal engagement section 1635 and diagnostic extension 1620 may position the tip of diagnostic extension 1620 and the diagnostic elements within diagnostic extension 1620 into a desired position or within a range of desired positions. For example, ear canal engagement section 1635 may have a diameter similar to that of the ear canal to contact all walls of the ear canal and thus, provide initial stability by limiting motion of the device when inserted. Or the ear canal engagement may be undersized relative to the canal to allow an easier fit into the canal and/or allow the user more positional control over the engagement section and the diagnostic extension. A user may subsequently adjust the device to position diagnostic extension 1620 based on the initial position provided by ear canal engagement section 1635 and further limited by the shape of diagnostic extension 1620 (i.e., the bends in the tubing of diagnostic extension 1620 maintain some distance between the diagnostic elements and a particular ear canal wall). This may help the device to optimize the diagnostic data capture. When the user is optimizing the position, the features incorporated into the device generally help to stabilize the device and help the user modify the position of diagnostic extension 1620 or diagnostic elements. This positioning of the device may apply to any of the configurations described herein as allowing a user to modify the position of diagnostic extension 1620 or diagnostic elements. These configurations may generally include any device having flexibility or motion enabled between the device components and the ear anatomy, which is based on the stiffness of the materials and how closely components are shaped to the specific person's anatomy.

Figure 17:
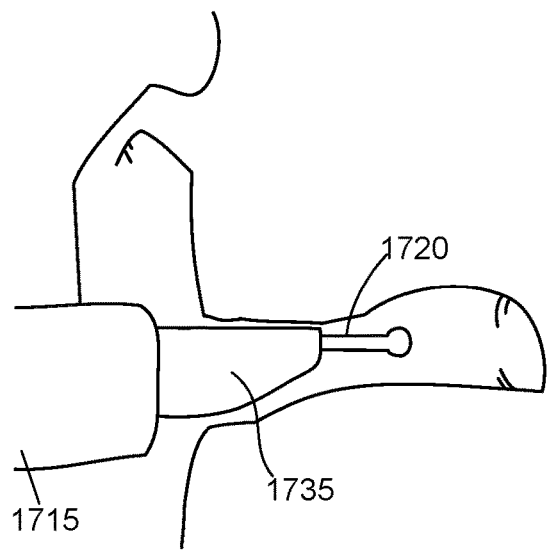
FIG. 17 depicts an ear canal engagement section that is shaped to the curvature of the inferior canal wall, in accordance with at least one embodiment.

FIG. 17 depicts an ear canal engagement section that is shaped to the curvature of the inferior canal wall, in accordance with at least one embodiment. Ear canal engagement section 1735 is coupled to body 1715. In some embodiments, ear canal engagement section 1735 is shaped to the curvature of the inferior canal wall that bends or curves up or superiorly as the canal moves medially, inward. For example, the radius of the tube of ear canal engagement section 1735 may decrease towards the distal end of ear canal engagement section 1735 on one side of the tube while the radius on the other side of the tube remains constant. Diagnostic extension 1720 may be positioned offset from the center axis of ear canal engagement section 1735's tubing (e.g., more superiorly or upward when the device is located within the user's ear).

Figure 18A:
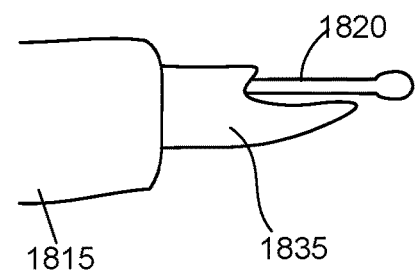
FIGS. 18A-B depict an ear canal engagement section having a first portion extending further into the ear canal than a second portion, in accordance with at least one embodiment.
Figure 18B:
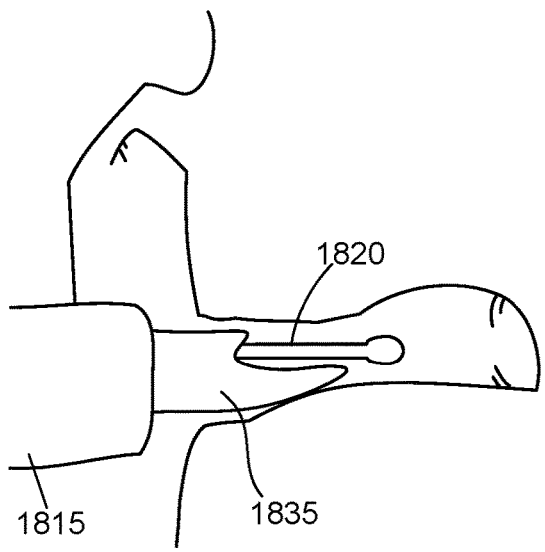

FIGS. 18A-B depicts an ear canal engagement section having a first portion extending further into the ear canal than a second portion, in accordance with at least one embodiment. FIG. 18A depicts part of a diagnostic device (i.e., from body 1815 towards the tip of diagnostic extension 1820) and FIG. 18B depicts the part of the diagnostic device situated within an ear. The diagnostic device may include ear canal engagement section 1835. In some embodiments, ear canal engagement section 1835 may include at least two portions, where a first portion contacts and extends from a portion of body 1815 and a second portion contacts the first part and is more proximal to body 1815 than the first portion (i.e., first portion extends further into the ear canal). This first portion may be referred to herein as a "sled" and the second portion may be referred to herein as an "upper portion" of ear canal engagement section 1835. When the device is worn by a user, the sled may extend further into the ear canal than the upper portion. Diagnostic extension 1820 may exit ear canal engagement section 1835 from the upper portion. Due to the structure of the upper portion not extending as far as the sled, there may be less material of the device around diagnostic extension 1820 (as opposed to the upper portion also extending around diagnostic extension 20 in parallel the sled). This may allow diagnostic extension 1820 to be positioned further into the ear canal, which narrows and can accommodate less and less of a device's materials as it narrows. Further, diagnostic extension 1820 may better conform to the canal because there is less material around the diagnostic extension for part of the length that may otherwise restrict motion. Diagnostic extension 1820 may be attached to ear canal engagement section 1835 where it exits from ear canal engagement section 1835 or diagnostic extension 1820 may be attached to a more proximal portion of the device (e.g., further back inside the device such as at body 1815) and all or a fraction of ear canal engagement section 1835 may be hollow. The hollow structure may enable diagnostic extension 1820 to float within ear canal engagement section 1835 and due to the reduction in movement constraint provided by the floating mechanism, encouraging diagnostic extension 1820 to be more likely to conform to a shape of the canal. A hollow ear canal engagement section 1835 may be utilized in the other embodiments (e.g., as depicted in other figures described herein). Additional examples of diagnostic devices having sleds are shown in FIGS. 64A-D, FIGS. 65A-D, and FIG. 66.

In some embodiments, the sled may be constructed to be at various sides of ear canal engagement section 1835. For example, the sled may be located at the upper half of ear canal engagement section 1835 (e.g., the half that is constructed to be closer or in the direction of an over ear piece coupled to body 1815 via a post) and the shorter, second portion may be at the bottom of ear canal engagement section 1835. In another example, the sled may be positioned at the side of ear canal engagement section 1835 such that, when the device is worn by the user, the sled is closer to the anterior wall of the ear canal and the shorter portion closer to the posterior wall. In some embodiments, ear canal engagement section 1835 has a cross section that is oval shaped. This oval shape may fit into an ear canal in an orientation that does not enable rotation once inserted into the canal (i.e., at least some portions of the ear canal are oval in shape and thus, limit the movement of an oval-shaped ear canal engagement section within it). The oval shaped ear canal engagement section may have a minor axis length that is substantially equivalent to the width of the ear canal (e.g., 5-10 mm) and a major axis substantially equivalent to the height of the ear canal (e.g. 6-13 mm), both referring to the smallest dimension segment of the ear canal engaged by the superior and inferior segments of the device. These may occur at different lengths into the canal. For example, the superior canal engagement may contact the superior wall near the entrance to the canal while the inferior segment of the canal engagement may contact the inferior wall at a position further into the canal than the superior segment, where the canal becomes smaller. In this instance, the major axis is from the superior wall contacting the superior engagement section to the inferior wall further into the canal which is contacts the inferior engagement section.

In some embodiments, ear canal engagement section 1835 has a round cross section, a diameter that is smaller than the ear canal (e.g., no more than 10 mm), and is coupled to a handle that may be held by a user, allowing the user to rotate the device and ear canal engagement section within the ear canal. The longer inferior segment of the canal engagement helps engage with the canal and stabilize and position the device in the canal and limits or prevents inferior rotation. Further, the shorter superior segment may help stabilize and position the device and engagement section, but also may allow the engagement section, and therefore diagnostic extension 1820, to be rotated up and be angled superiorly in the canal which may match the upward direction of the inferior wall. Thus, the configuration of the ear canal engagement helps to achieve a desired position of the diagnostic extension 1820 to capture diagnostic information, such as images or video, from the eardrum. This may be enabled more when smaller size (height or width) canal engagement sections, or attachments, are used relative to the cross section size of the canal.

Figure 19:
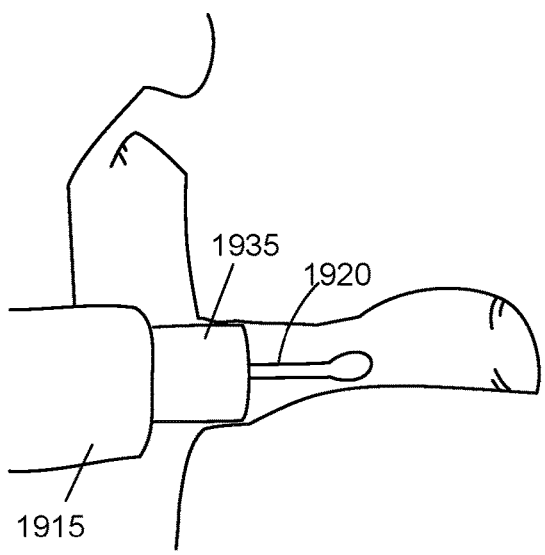
FIG. 19 depicts an ear canal engagement section, in accordance with at least one embodiment.

FIG. 19 depicts an ear canal engagement section, in accordance with at least one embodiment. Ear canal engagement section 1935 is coupled to body 1915. In some embodiments, ear canal engagement section 1935 functions similar to a stop. Ear canal engagement section may be cylindrical in shape (e.g., a tube) with a diameter that is sized to fit within the opening of the ear canal but not past a certain point of the ear canal. The cross section of ear canal engagement section 1935 may be circular or oval, where length along the major axis is sized to fit within the opening of the ear canal but not past a certain point of the ear canal. The dimension of ear canal engagement section 1925 in this direction of the major axis of the canal may be 6-9 millimeters long (or even smaller for infants, for example 3-5 mm) such that it is small enough to fit into the entrance of the ear canal but is stopped by the narrowing walls of the ear canal as the device is further inserted into the canal. For example, the inferior-superior direction of the canal may be smaller than the infer-superior height of ear canal engagement section 1935, which prevents or limits ear canal engagement section 1935 from moving further into the ear canal.

Figure 20:
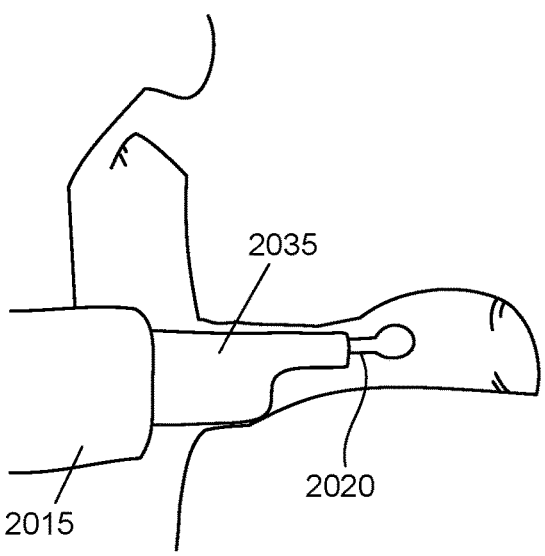
FIG. 20 depicts a stepped configuration of an ear canal engagement section, in accordance with at least one embodiment.

FIG. 20 depicts a stepped configuration of an ear canal engagement section, in accordance with at least one embodiment. In some embodiments, a distance from the outer surface to an axis running through ear canal engagement section 2035 is changing along the length of ear canal engagement section. The changing distance may be such that the one side of ear canal engagement section 2035 is stepped. The axis running through ear canal engagement section 2035 may not necessarily be a central axis. For example, as shown in FIG. 20, a horizontal axis may run through the center of diagnostic extension 2020 and towards the outer perimeter of ear canal engagement section 2035 and body 2015. This axis is offset from the center of ear canal engagement section 2035 and body 2015. In one example, two thirds of the length of a cylindrical ear canal engagement section 2035 a first may have a first diameter (e.g., 8 millimeters) and the remaining third of the length of the cylindrical ear canal engagement section that extends further into the ear (i.e., the distal end of ear canal engagement section 2035) may have a second diameter (e.g., 4 millimeters). Ear canal engagement section 2035 may be configured such that, when the device is inserted into the ear, the superior or higher part of ear canal engagement section 2035 extends further into the canal, as it is longer than a lower or more inferior part of ear canal engagement section 2035. This configuration can be used in varying directions, for example, a longer posterior or back of ear canal engagement section 2035 vs a shorter more anterior or front portion. For example, the proximal end of ear canal engagement section 2035 may have a given diameter along a length of at least 50% of the total length of ear canal engagement section 2035, with the remaining length towards the distal end having a smaller diameter. This configuration may help position diagnostic extension 2020 at a pre-determined location that is further into the ear canal. This configuration may conform to the anatomy. For example, the inferior wall of the canal curves superiorly, so the longer superior part of ear canal engagement section 2035 fits and the shorter length of the inferior part of ear canal engagement section 2035 also fits. That is, because of the smaller diameter at the distal end of ear canal engagement section 2035 and the axis of ear canal engagement section being offset by a certain distance from the central axis of the ear canal (e.g., offset by 2 millimeters) at least relative to the axis of the entrance of the ear canal, the ear canal engagement section 2035 is able to fit within an ear canal whose walls not only narrow but also narrow upward. It is preferred that ear canal engagement section 2035, at least in half of ear canal engagement section 2035 (e.g., a half facing the superior wall of the ear canal when the device is inserted), is hollow, and diagnostic extension 2020 is connected further back inside the device from where it exits ear canal engagement section 2035. This structure may allow diagnostic extension 2020 to move more freely to conform to the ear canal.

Figure 21:
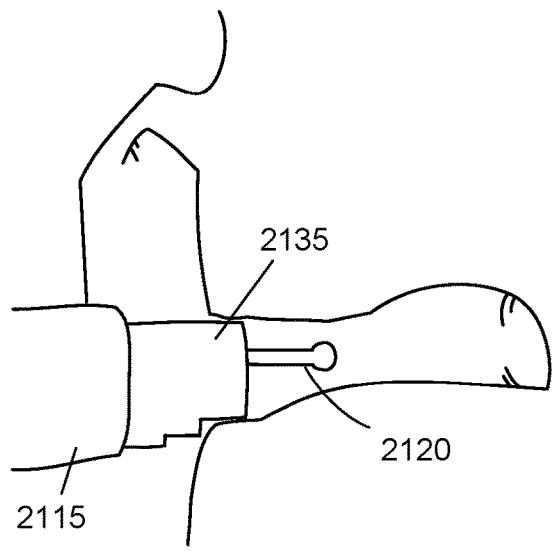
FIG. 21 depicts a multi-stepped configuration of an ear canal engagement section, in accordance with at least one embodiment.
Figure 22:
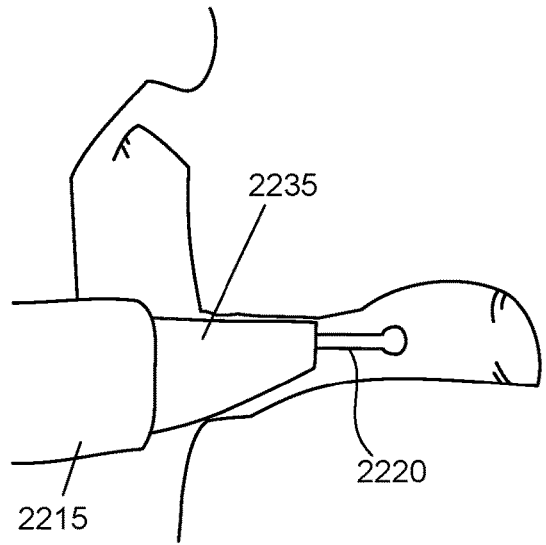
FIG. 22 depicts a continuously tapered configuration of an ear canal engagement section, in accordance with at least one embodiment.
Figure 23:
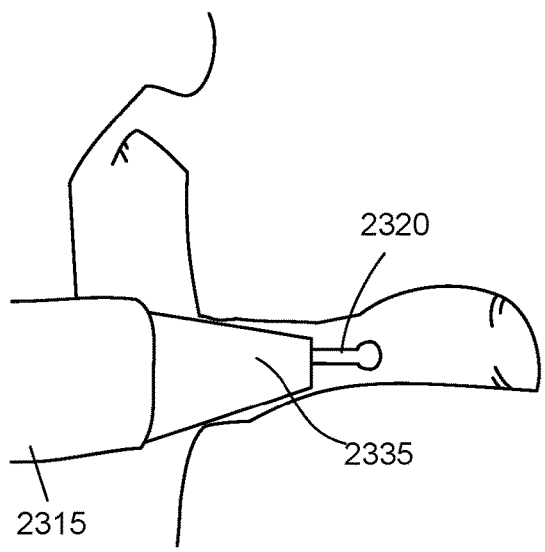
FIG. 23 depicts a continuously tapered configuration of an ear canal engagement section encouraging a central position of a diagnostic extension, in accordance with at least one embodiment.

FIG. 21 depicts a multi-stepped configuration of an ear canal engagement section, in accordance with at least one embodiment. FIG. 22 depicts a continuously tapered configuration of an ear canal engagement section, in accordance with at least one embodiment. FIG. 23 depicts a continuously tapered configuration of an ear canal engagement section encouraging a central position of a diagnostic extension, in accordance with at least one embodiment. In some embodiments, as shown in FIG. 21, ear canal engagement section 2135, coupled to body 2115, may include a stepped outer surface. Each step of ear canal engagement section 2135 may correspond to a diameter or height of a certain age range's average ear canal height at the entrance of the canal. For example, a first step that is most distal on ear canal engagement section 2135 may have a height of 5 millimeters to enable insertion into the ear canal, and which may contact at least the superior and inferior walls of the ear canal, of a person under the age of 3 for example, or a person with smaller size ear canals, a second step that is adjacent to the first step may have a height of 7 millimeters to enable insertion into the ear canal, and which may contact at least the superior and inferior walls, of a person within the ages of 3-8 years of age for example, or a person with medium size ear canals, and a third step that is adjacent to the second step may have a height of 10 millimeters to enable insertion into the ear canals, and which may contact at least the superior and inferior walls, of a person older than 8 years of age for example, or persons with larger size canals. Age ranges are meant as examples only, as anatomy varies within and across age groups. An engagement section with an even shorter first step, for example 3-4 mm in height, may be used for infants. In each case, a larger height or step or part of the body may serve as a stop to prevent further insertion.

Similarly, ear canal engagement section 2235 may be continuously tapered, as shown in FIG. 22, to fit a more continuous range of ear anatomy sizes or user ages. The tapering may occur on one side of ear canal engagement section 2235. For example, with reference to FIG. 22, an axis may run through ear canal engagement section 2235 that is offset from a central axis exiting body 2215. A distance from the axis to one side of ear canal engagement section 2235 along the length of ear canal engagement section 2235 may be constant (e.g., 2 millimeters) while a distance from the axis to another side is decreasing from 8 millimeters to 2 millimeters towards the distal end of ear canal engagement section 2235. The structure depicted in FIGS. 21 and 22 may help to bias diagnostic extension 2120 or 2220 towards one side of an ear canal. For example, diagnostic extension 2120 may be positioned towards the superior wall of the ear canal due to the greater distance from an axis running central to diagnostic extension 2120 to an outer surface of ear canal engagement section 2135, where this outer surface is configured to touch the inferior wall of the ear canal (i.e., the device is constructed with this outer surface facing the bottom of the device). In some embodiments, an ear canal engagement section may be tapered on more than one side. For example, as depicted in FIG. 22, ear canal engagement section 2235 is tapered on at least two sides. The slope of tapering may be the same on either side or one side may have a greater slope of tapering than another. The slope of tapering may affect the position at which diagnostic extension 2220 is biased. For example, since the inferior (lower) wall of the ear canal anatomy curves upward with a greater slope than the superior (upper) wall of the ear canal, one side of ear canal engagement section 35 may taper with a larger slope than the other such that the tapering of ear canal engagement section 35 may conform with the anatomy of the ear canal.

In some embodiments, portions of body 2215 of the device, including ear canal engagement section 2235, may have a width that is equal to or less than the width of the ear canal (e.g., less than 10 millimeters) or than the width of the portion of the device configured to be extended into the ear canal. For example, a portion of ear canal engagement section 2235 or body 2215 that is outside of the canal when the device is worn on the user may have a width of 3 millimeters. Reducing the dimensions of portions of body 2215 would limit interference with the tragus and because contact is avoided, limit possible forces from the tragus that may push the device in a less desirable position. In some embodiments, a portion of the device outside the canal is wider than the canal or engagement section of the device in the canal; the portion may be constructed from a flexible material or moldable material to reduce impact from contact with the tragus or other anatomy in the visible outer ear outside of the ear canal. The device may be composed of various components that may either be rigid, flexible, soft, or hard. In some embodiments, a portion of body 2215 lateral to the canal when the device is in place (e.g., near the connection between two segments composing body 115 in FIG. 1) is wider than the ear canal and another portion of body 2215 (e.g., the portion including ear canal engagement section 2235) has a width equivalent or smaller than to the width of the ear canal. If the device is wider outside the canal, and thus potentially subject to forces from the tragus, the width of ear canal engagement section 2235 in a substantially anterior-posterior direction (when the device is worn by the user) may be similar to the width of the ear canal. This would limit motion of the device in these directions, which may be the direction of force exerted by the tragus. Ear canal engagement section 2235 may be tapered so that a particular position of diagnostic extension 2220 is achieved. In some embodiments, diagnostic extension 2220 is constructed such that it extends from a side of ear canal engagement section 2235 that is a different side at which tapering occurs. For example if ear canal engagement section 2235 is tapered out on the anterior side (when the device is worn by the user), diagnostic extension 2220 may be located at a posterior position within the ear canal. Multiple directions of tapers or steps can be configured. The tapered structure of ear canal engagement 2235 allows diagnostic extension 2220 to extend further into the canal as the height of ear canals increases (i.e., with different sizes of ears or as persons age). This may be especially useful for capturing diagnostic information about children's ears. The tapers or steps may limit the amount of further insertion as the canal size changes while a patient ages or among different users. This may be another benefit for capturing diagnostic information about children's ears as their ear sizes are changing as they age, and a user may not have to own multiple devices to capture diagnostic information about differently sized ears. Rather, a user may own a single device having tapered ear canal engagement section 2235 which may accommodate more than one ear canal size.

Figure 24:
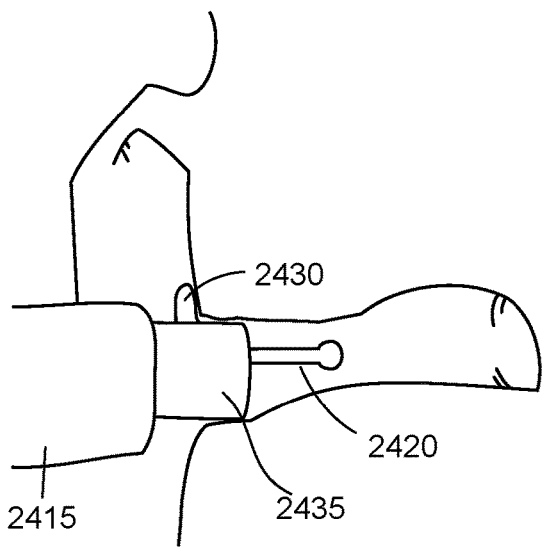
FIG. 24 depicts an ear canal engagement section having a stop contacting the ear outside of the canal at at least one point, in accordance with at least one embodiment.

FIG. 24 depicts an ear canal engagement section having a stop contacting the ear outside of the canal at at least one point, in accordance with at least one embodiment. Ear canal engagement section 2435 is coupled to body 2415. In some embodiments, ear canal engagement section 2435 includes stop 2430 contacting the ear outside of the ear canal. Stop 2430 may be configured to contact the visible outer ear above the entrance of the ear canal. In some embodiments, stop 2430 may be tall and narrow such that height of stop 2430 is 30-50% the height of ear canal engagement section 2435 and 20-40% the width of ear canal engagement section 2435. For example, stop 2450 may be tall and narrow with a height of 4 mm (e.g., contacting 4 mm above the ear canal entrance) and a width of 1.5 mm. Ear canal engagement section 2435, although depicted as having a constant thickness along its length, may alternatively or additionally have a tapered side along at least some of its length (e.g., as shown in FIG. 22 or 23). The stop may be rigid or plastic or rubber. The height of stop 2430 may be 3-10 millimeters and the width may be no wider than ear canal engagement section 2435. In some embodiments, the width of stop 2430 is wider than ear canal engagement section 2435, and the material of at least the portion of stop 2430 wider than ear canal engagement section 2435 may be flexible. Although stop 2430 is depicted as connected to the upper side of ear canal engagement 2435 (i.e., in a superior direction or in the same direction as a portion of body 2415 may bend towards an optional over ear piece), stop 2430 may be connected to the bottom side of ear canal engagement 2435 (i.e., in an inferior direction). This inferior stop may extend down and align in the intertragic notch.

Figure 25:
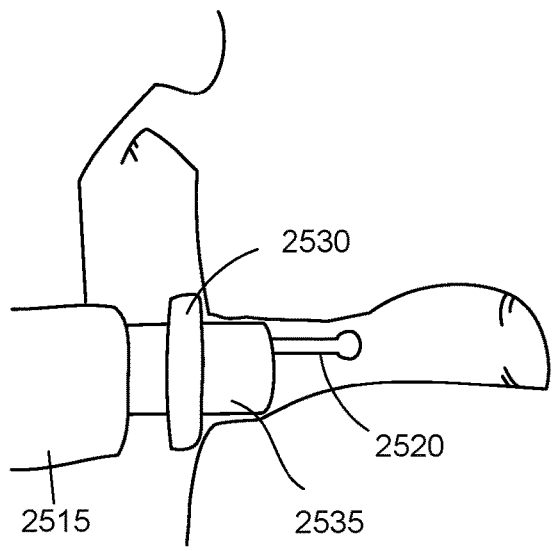
FIG. 25 depicts an ear canal engagement section having a stop contacting the ear outside of the canal at at least two points, in accordance with at least one embodiment.

FIG. 25 depicts an ear canal engagement section having a stop contacting the ear outside of the canal at at least two points, in accordance with at least one embodiment. Ear canal engagement section 2535 is couple to body 2515. In some embodiments, ear canal engagement section 2535 includes stop 2530 that contacts the outside of the ear canal in both superior and inferior directions. Stop 2530 may be flexible. Ear canal engagement section 2535 may extend in the anterior or posterior directions (i.e., side to side with reference to top and bottom of ear canal engagement 2535) in addition to inferior and superior directions. Or the width of stop 2530 may be equal to or less than the width of the ear canal or the ear canal engagement section.

Figure 26:
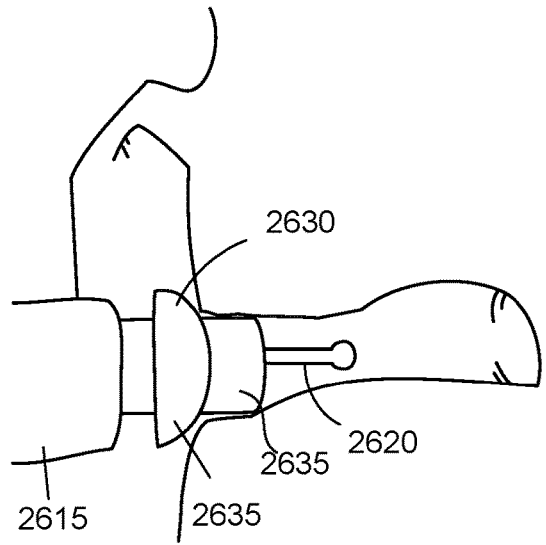
FIG. 26 depicts an ear canal engagement section having a stop with a semi-sphere shape, in accordance with at least one embodiment.

FIG. 26 depicts an ear canal engagement section having a stop with a semi-sphere shape, in accordance with at least one embodiment. Ear canal engagement section 2635 is coupled to body 2615. Ear canal engagement section 2635 may include a cylindrical tube and stop 2630 located midway along the length of the cylindrical tube. Stop 2630 may be a hollow or solid semi-sphere. Stop 2630 may be made of a flexible or rigid material. The diameter of stop 2630 may be greater than the width or height of the ear canal (e.g., greater than 5-13 millimeters depending on canal size and direction). The height of ear canal engagement section 2635 may be equivalent to the height of the ear canal (e.g., 6-13 millimeters). In some embodiments, stop 2630 may seal or partially seal the ear canal to for the device to capture acoustic or pressure diagnostics (e.g., as described with reference to FIG. 10). The stop may be circular or oval in shape. For example, the stop may have a height greater than or substantially equivalent to the ear canal and a width equivalent to or less than the width of the canal.

Figure 27:
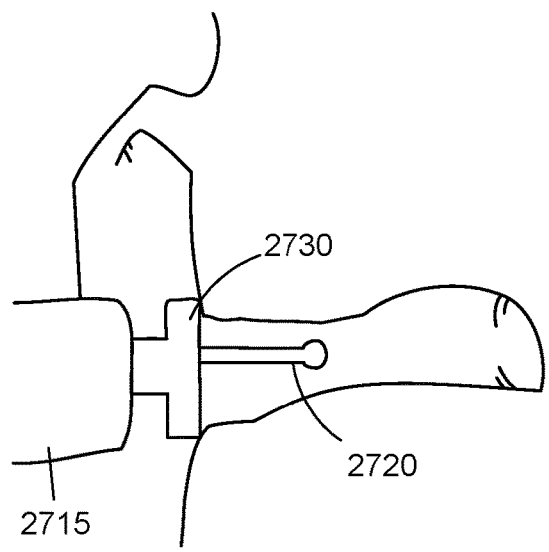
FIG. 27 depicts a device with a stop and without an ear canal engagement section, in accordance with at least one embodiment.

FIG. 27 depicts a device with a stop and without an ear canal engagement section, in accordance with at least one embodiment. Stop 2730 may be coupled to body 2715 and diagnostic extension 2720 may be attached to stop 2730. Alternatively, diagnostic extension 2720 may be attached to body 2715 and travel through a hollow stop 2730 and exit in the same direction in which the portion of body 2715 is extended (e.g., towards the ear canal when the device is worn by the user). Without an ear canal engagement section, the device may provide more room for moving diagnostic extension 2720 within the ear canal.

FIG. 28 depicts a device with a body connected to an over ear piece via a post, in accordance with at least one embodiment. A side view of a device is depicted in FIG. 28 with a cross section of the ear canal engagement section. Over ear piece 2805 may be coupled to post 2810, which is further coupled to body 2815. Body 2815 includes ear canal engagement section 2835, which includes channel 2850 for a diagnostic extension to float or move. Body 2815 is further coupled to diagnostic extension 2820. Although not depicted, the device may contain wires to transport diagnostic data, light, power, or any matter used to diagnose an ear or mouth or capture diagnostic information about the ear or mouth.

Attachments to a device described herein can be included within a diagnostic kit and used to adjust for sizes of varying anatomies (e.g., differently sized ears). In some embodiments, attachments fit over ear canal engagement section 2835. The attachments may have functionality or structure similar to that of ear canal engagement section 2835 or a stop. The dimensions of the attachments may be larger than those of ear canal engagement section 2835 to fit over ear canal engagement section. The attachments may include a hole or channel through which the device may fit through. For example, the attachments may include a channel through which diagnostic extension 2820 may fit through. The attachments may be structured like a sleeve or cover under which ear canal engagement section 2835 of the device may fit. In some embodiments, a diagnostic kit includes attachments of varying sizes to fit differently sized ears. The attachments may be a material different from the material with which ear canal engagement section 2835 of the device is composed. For example, the attachments may be composed fully or partially with silicon to provide a soft interface for contacting tissue. In some embodiments, the attachments may connect to the device through a snap fit. For example, the inner surface of the attachments made include grooves or protrusions that couple with respective protrusions or grooves on the surface of the device (e.g., on the surface of ear canal engagement section 2835) to secure the attachment to the device. In some embodiments, a diagnostic kit may include a diagnostic device including over ear piece 2805, post 2810, body 2815, diagnostic extension 2820, and multiple attachments. Body 2815 of this device may be a basic tube in structure, or take any other shape, and include only the more proximal section of the body without the distal section which includes anatomical interfaces such as a stop or ear canal engagement section. The attachments within the kit may then include such anatomical interfaces and attach to the body of the device.

FIGS. 29-31 depict various attachments that fit onto the device of FIG. 28, in accordance with at least one embodiment. The attachments are shown as sleeves 2935, 3035, and 3135 that may slide onto body 2815 of the device of FIG. 28, but the attachments can alternatively or additionally be configured to couple to body 2815 via mechanical attachment means, including attracting magnets. The attachments may be made to fit different sizes of ears or ear canals and varying patient ages. The attachments include channels 2945, 3035, and 3145 through which ear canal engagement 2835 may fit through. The attachments provide stops (e.g., stop 2930, 3030, or 3130) to prevent diagnostic extension 2820 from entering the canal beyond a predetermined depth. The attachments may be configured to be equivalent to or less than an ear canal's width (e.g., 10 millimeters or less). The attachments may maintain a desired position of diagnostic extension 2820 in a predetermined position (e.g., biased towards the superior wall of the ear canal). This position may be obtained using any size of the attachment, as the position of diagnostic extension 2820 may depend primarily or entirely upon its connection to body 2815 or amount of movement offered by channel 2850 with a diameter larger than the tubing of diagnostic extension 2820. Diagnostic extension 2820 may have different positions than shown in FIG. 28, including a central position or an inferior position or angled position within body 2815 relative a central axis of body 2815. In some embodiments, diagnostic extension 2820 is configured with a superior angle, or a posterior position, or a posterior and superior position. Such configurations may be achieved by coupling diagnostic extension 2820 to body 2815 where the central axis of diagnostic extension 2820 is offset or angled from body 2815. For example, for a posterior and superior position, the central axis of diagnostic extension may be offset from the central axis of body 2815 by 10% of the diameter, or a height or width dimension, of body 2815 and angled between 10-20 degrees from the central axis of body 2815. Channel 2850 may provide space to accommodate for the offset or angling of diagnostic extension 2820 within body 2815 or the channel may be configured with the corresponding offset or angle. In some embodiments, the attachments are structured so that when connected to the device, the top of the ear canal engagement of the attachment is closer to the axis of the diagnostic extension than the bottom of the ear canal engagement section of the attachment, which may help maintain a superior position of the extension in the ear canal.

In some embodiments, the attachments have a height where the distance between the top of the attachment and the top of body 2815 is smaller than the distance between the bottom of the attachment and the bottom of body 2815. That is, attachments extend lower than body 2815 extends. Accordingly, the attachments may add more material inferiorly to ear canal engagement section 2835 of the device, which may help maintain a superior position of the extension within the ear canal. This may be evident with attachments with taller ear canal engagement sections for larger size ear canals, which are substantially taller than the ear canal engagement of the base device, which is preferably configured with a height that will fit into the smallest ear canals, for example into infants and newborns. The attachments may be configured so that the length of diagnostic extension 2820 may vary depending on the attachment coupled to the device. For example, a longer diagnostic extension may be needed larger ears. A first attachment may cover a larger portion of the length of diagnostic extension 2820, thus shortening the positioning of the extension that may be inserted to the ear canal. That is, an attachment may act as a stop that prevents the device and thus, diagnostic extension 2820, from moving further into the ear canal.

In some embodiments, the larger the attachment or greater area of the distal end of body 2815 that the attachment covers, the shorter diagnostic extension 2820 may reach into an ear canal. The attachments may be configured to allow varying lengths of insertion into the ear canal. For example, a longer attachment with a longer ear canal engagement length may have a stop that is positioned more proximally on the device when the attachment is in place. This results in a longer section of ear canal engagement inserted into the canal and thus allows the diagnostic extension to reach further into the canal. Another example is a shorter attachment with a stop that is positioned more distally on the device when the attachment is in place, resulting in a shorter section of ear canal engagement inserted into the canal and thus the diagnostic extension does not reach as far into the canal. In another example, an attachment is configured to attached to the device so that a stop on the attachment is near or in front of (distal to) the superior segment of the ear canal engagement of the device and the ear canal engagement section of the attachment may extend in front of (more distal to) the ear canal engagement of the device, resulting in an even shorter reach of the diagnostic extension into the ear canal. This may be advantageous for newborns and infants with shorter ear canal lengths.

Figure 32:
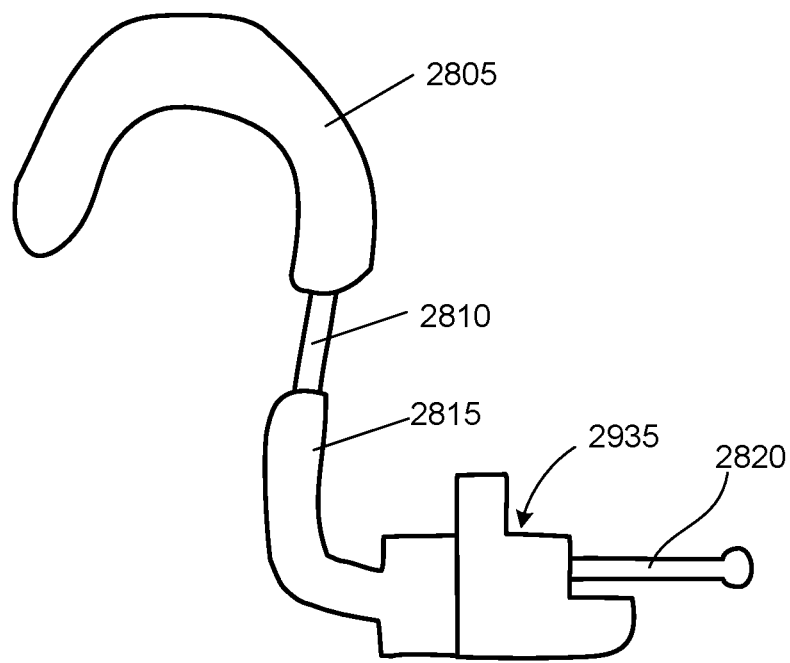
FIG. 32 depicts the attachment of FIG. 29 placed onto the device of FIG. 28, in accordance with at least one embodiment.
Figure 33:
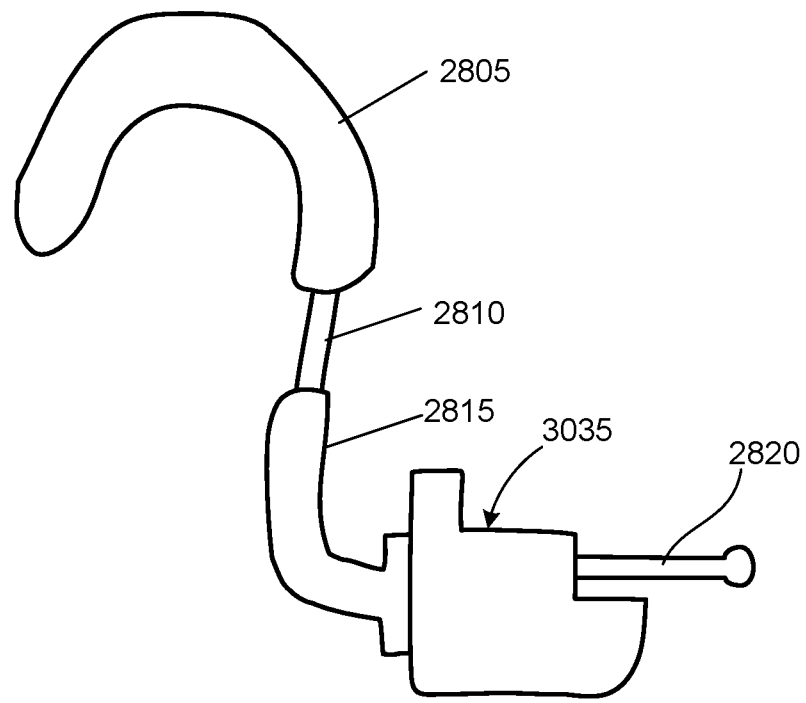
FIG. 33 depicts the attachment of FIG. 30 placed onto the device of FIG. 28, in accordance with at least one embodiment.

The attachments, enabling diagnostic extension 2820 to extend into the ear canal at varying distances, may be advantageous for capturing diagnostic information for children's ears, which are developing and changing shapes (e.g., the ear canal lengths) as a child ages. This is especially important for newborns and infants, as the ear canal grows from approximately 10 mm in length at birth to full length at approximately 1 year of age to a length of approximately 25 mm. In some embodiments, attachments may include varying widths and heights (e.g., varying oval shapes) to accommodate for varying widths and heights of ear canals. For example, although the length of ear canals may not vary substantially among varying ages greater than 1 year of age, the width and height of ear canals may vary significantly. Accordingly, attachments having varying widths and heights may accommodate for varying ear canal widths and heights. The attachment may include a stop, a tapered side, or a stepped side (e.g., similar to those of ear canal engagement sections described herein). The height or width of the attachment may vary depending on the location of a stop on the attachment. For example, positioning the stop at a first side of the attachment may cause the attachment to be taller than it is wide. Similarly, positioning the stop at a second side, adjacent to the first side, may cause the attachment to be wider than it is tall. FIGS. 32 and 33 depict attachments of FIGS. 29 and 30, respectively, placed onto the device of FIG. 28, in accordance with at least one embodiment and show different size canal engagements and different stop locations, enabling different lengths of insertion into the ear canal.

Figure 34:
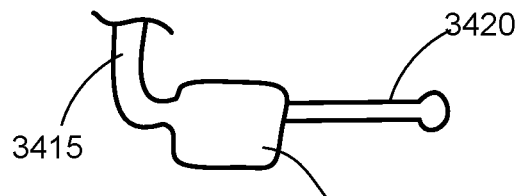
FIG. 34 depicts an ear canal engagement section with the end at an equal distance in all locations of the canal, in accordance with at least one embodiment.

FIG. 34 depicts an ear canal engagement section with the end at an equal distance in all locations of the canal, in accordance with at least one embodiment. Ear canal engagement 3435 houses diagnostic extension 3420 and is coupled to body 3415. In some embodiments, a diagnostic device described herein has ear canal engagement section 3435 with the end at an equal distance in all locations of the canal (i.e. superior, inferior, etc.). This may be compared to an embodiment of a diagnostic device where ear canal engagement section 3435 has a longer inferior section. The diagnostic extension may be located in any position and at any angle, for example posterior, anterior, superior, inferior or an angle such as a superior angle. The engagement section may be hollow, have a hollow section offset and/or angled to the axis of the ear canal engagement, and allow the diagnostic extension to move within the canal engagement. Or the diagnostic extension may be attached at the exit point from the ear canal engagement at the desired position/orientation and angle.

Figure 35:
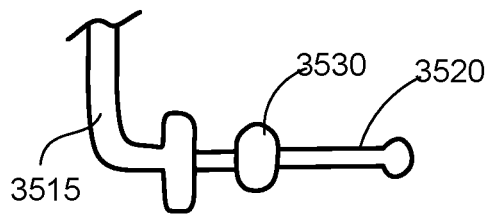
FIG. 35 depicts a device that does not include an ear canal engagement section prior to an attachment being added, in accordance with at least one embodiment.

FIG. 35 depicts a device that does not include an ear canal engagement section prior to an attachment being added, in accordance with at least one embodiment. In some embodiments, a diagnostic device does not include ear canal engagement section 3535 (e.g., this configuration may couple to an attachment that serves as an ear canal engagement section). In some embodiments, a diagnostic device lacking ear canal engagement section 35 may include stop 3530. Stop 3530 may be a spherical or oval shaped protrusion from diagnostic extension 3520, which is coupled to body 3515. Stop 3530 may have a width or diameter that is larger than the width of an ear canal. Stop 3530 may prevent a user from inserting diagnostic extension 3520 past a certain depth (i.e., the distance from stop 3530 to the distal tip of diagnostic extension 3520) within the ear canal. For example, the stop may serve as a safety stop if the user uses the device without attaching an attachment, which may include the most desired stop position and size. In some embodiments, attachments as described with reference to FIGS. 29-31 may couple to body 3515 and fit over stop 3530. For example, attachments have a channel having height and width greater than the height and width of step 3530.

Figure 36:
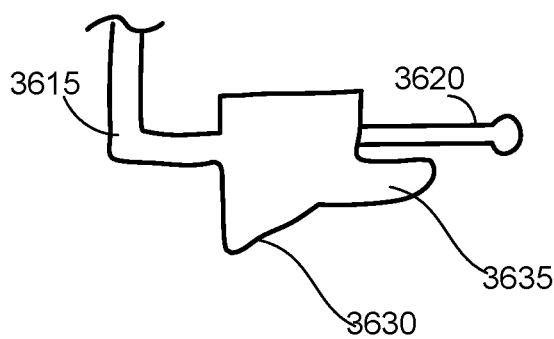
FIG. 36 depicts a device with a body having a tapered stop on one side of the body, in accordance with at least one embodiment.
Figure 38:
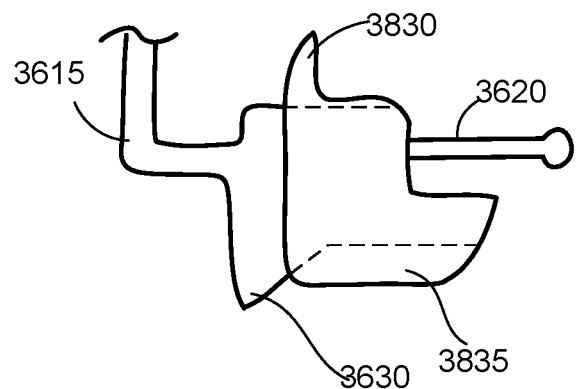
FIG. 38 depicts an attachment fitting onto the device of FIG. 36, in accordance with at least one embodiment.

FIG. 36 depicts a device with a body having a tapered stop on one side of the body, in accordance with at least one embodiment. In some embodiments, body 3615 is shaped to have tapered stop 3630, which may be located at the bottom of body 3615 (i.e., such that the tapered border is located near the anti tragus, intertragic notch, or lobule when the device is worn by the user). The tapered stop may prevent the device from being inserted into the ear canal past a distance, which may vary depending on the slope of the taper and height of the ear canal. For a given ear, a larger slope may prevent diagnostic extension 3620 from entering further into the ear canal than a smaller slope. For a given slope, diagnostic extension 3620 may enter farther into a taller ear canal than a shorter ear canal. An attachment to accommodate for an ear canal having a taller height is shown in FIG. 38. In FIG. 38, the attachment is configured to fit over part of the tapered stop 3630 (e.g., constructed like a sleeve with a channel through which body 3615 and diagnostic extension 3620 may fit through) and has a flat bottom surface to contact a flat inferior surface of the ear canal.

Figure 37:
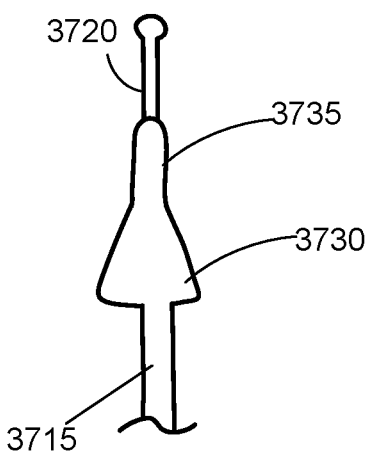
FIG. 37 depicts a device with a body having a tapered stop on two sides of the body, in accordance with at least one embodiment.

FIG. 37 depicts a device with a body having a tapered stop on two sides of the body, in accordance with at least one embodiment. In some embodiments, body 3715 may be tapered with decreasing width from the proximal end of body 3715 towards the distal end. This tapering may occur at two sides of body 3715. The two sides may be opposite from one another. For example, body 3715 may be constructed such that the two sides taper in directions orthogonal to both the directions in which diagnostic extension 3720 extends and in which body 3715 extends to connect to post 3710. This may, when the device is worn by a user, be the anterior-posterior direction with reference to the user's head. This taper may act as a stop based on the width of the canal. This is similar the configuration depicted in FIG. 36, which depicts a taper that forms stop 3730, the height of which may be based on the height of the canal, entering further into the canal for wider canal anatomy. In some embodiments, an attachment may be coupled to body 3715, where the attachment further includes one or more tapered stops such that the device with the attachment may contact walls of wider ear canals and prevent diagnostic extension 3720 from extending a certain distance within an ear canal. Attachments may also have an additional stop, for example a stop that extends only on a posterior direction, or have only a stop that extends in the superior direction and not include a wider a wider taper for wider canals.

FIG. 38 depicts an attachment fitting onto the device of FIG. 36, in accordance with at least one embodiment. The attachment includes stop 3830 and ear canal engagement section 3835. The attachment includes a channel through which body 3615 may fit within and a hole through which diagnostic extension 3620 may fit through. Attachments can be flexible, compressible, soft, or rigid. In one example, body 3615 of the device is flexible and the attachment is more rigid, providing structure for the part of the device that engages with the ear canal and positions the device and diagnostic extension 3620. The flexible device and body 3615 may better conform to the variety of anatomy that may be encountered in the outer visible ear or elsewhere (e.g., the mouth).

Figure 39A:
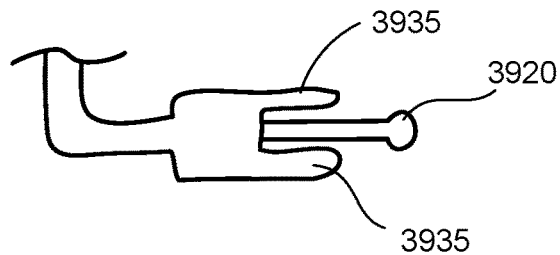
FIGS. 39A-B depict ear canal engagement sections including openings to enable side-to-side motion of a diagnostic extension, in accordance with at least one embodiment.
Figure 40A:
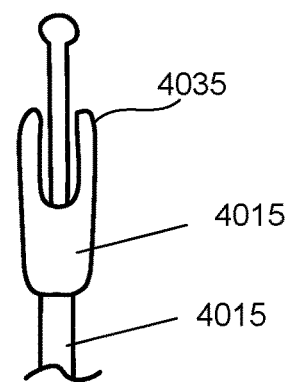
FIGS. 40A-B depict ear canal engagement sections including openings to enable up-down motion of a diagnostic extension, in accordance with at least one embodiment.
Figure 39B:
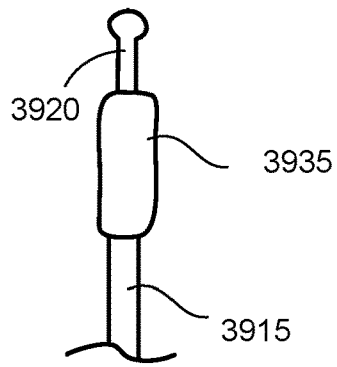
Figure 40B:
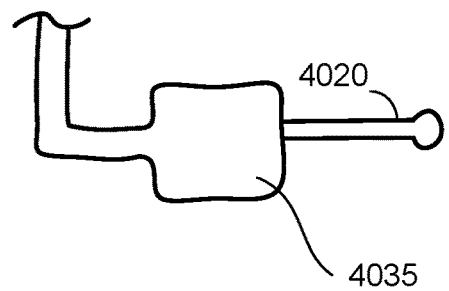

FIGS. 39A-B depict ear canal engagement sections including openings to enable side-to-side motion of a diagnostic extension, in accordance with at least one embodiment. FIGS. 40A-B depict ear canal engagement sections including openings to enable up-down motion of a diagnostic extension, in accordance with at least one embodiment. In some embodiments, ear canal engagement sections 3935 and 4035 allow more motion of diagnostic extensions 3920 and 4020, respectively, side to side (e.g., FIGS. 39A-B) or up and down (e.g., FIGS. 40A-B). The structure of ear canal engagement section 3935 or 4035 that may allow this movement includes an opening within body 3915 or 4015 that is bordered on two, opposing sides by extensions of ear canal engagement section 3935 or 4015, respectively. Diagnostic extension 3920 or 4020 may exit respective bodies 3915 or 4015 through this opening and be bordered by these extensions. The extensions of the ear canal engagement section may flexible or rigid. They may be approximately half the length of ear canal engagement section 35, or ¾ length or the full length. Attachments may fit over body 3915 or 4015. The openings may enable larger attachments to provide wider or taller boundaries for diagnostic extension 3920 or 4020 than a smaller attachment. If body 3915 or 4015 is continuous as shown in the figures, including the ear canal engagement section prior to an attachment being attached, it may be sized for a small ear canal width (e.g., 3-5 millimeters to fit infants) if it is intended to enter the canal. Fittings or attachments can then fit over body 3915 or 4015 to better fit and position devices into larger canals. Diagnostic extension 3920 or 4020 at the exit of ear canal engagement section 3935 or 4035 may consequently have less relative room to move in larger canals than in smaller canals in the direction of the canal engagement extensions but have the same relative room to move in the direction of the openings. In some embodiments, larger attachments may cause the motion of diagnostic extension 3920 or 4020 to be limited by a smaller body within the attachment. Alternatively, the device may be configured with only body 3915 or 4015 that does not include the distal ear canal engagement section and attachments are provided to connect to body 3915 or 4015 that include the distal ear canal engagement sections. The configurations in FIGS. 39A-B and 40A-B allow bigger attachments to fit over the body and more mobility for a diagnostic extension in bigger attachments in the direction where the internal body is cut away (i.e., due to the opening). The openings would be provided in whatever direction it is preferred to allow more motion of a diagnostic extension.

Figure 41:
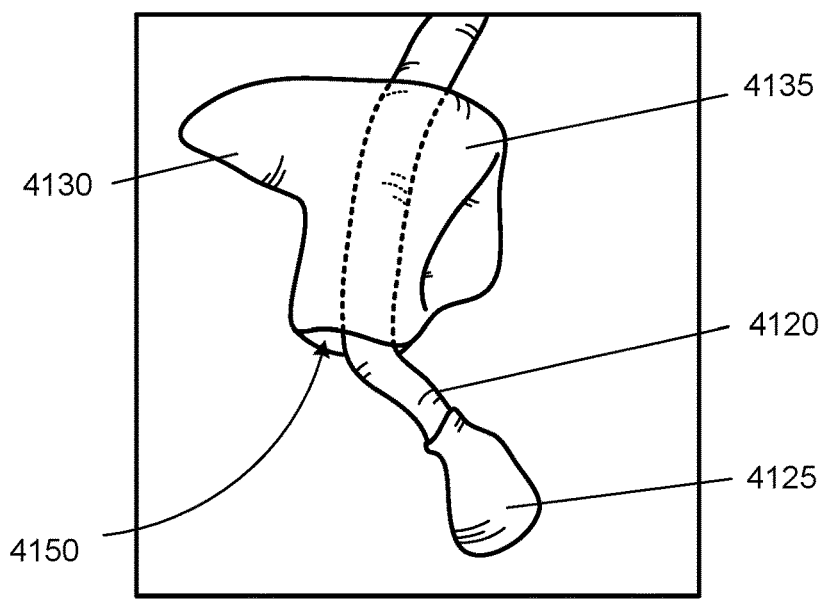
FIG. 41 depicts a diagnostic extension within an ear canal engagement section having one or more hollow sections, in accordance with at least one embodiment.

FIG. 41 depicts a diagnostic extension within an ear canal engagement section having one or more hollow sections, in accordance with at least one embodiment. In some embodiments, diagnostic extension 4120 includes a bulb at or near the tip of diagnostic extension 4120. The tip may be configured in a variety of shapes, such as a cylinder or oval or sphere, which has a larger cross section than the more proximal segment of the diagnostic extension. Bulb may refer to a shape with a larger cross section than a more proximal segment of the diagnostic extension (e.g., larger than the cross section of the tube connected to the bulb). The bulb may have a small diameter relative to the diameter of the ear canal or ear canal engagement section 4135. The bulb may have a diameter that is substantially equivalent to that of the ear canal or ear canal engagement section 4135. Diagnostic extension 4120 may be shaped similar to an ear speculum or cone. Diagnostic extension 4120 having an ear speculum shape may include a bulb or larger sized section at the tip of diagnostic extension 4120. In some embodiments, diagnostic extension 20 floats within a section of the device (e.g., within channel 4150), connected further back inside the device from where it exits, allowing diagnostic extension 4120 to move further with less bending as it conforms to the shape of the canal, than if it connected at the point where it exits body 4115 of the device, in this case ear canal engagement section 4135 of body 4115 of the device. This may allow diagnostic extension 4120 to move without the tip being bent to such an angle that it is out of alignment with the eardrum or is in less than ideal alignment. Various configurations of hollow body 4115 sections or ear canal engagement sections 4135 can be created. The part of the device where diagnostic extension 4120 is floating within, may only be hollow, or open around diagnostic extension 4120, in a more superior location of the device, or it may fully open and only have thin walls to help position the device but in this configuration, allow the most free motion of diagnostic extension 4120.

In some embodiments, diagnostic extension 4120 is constructed with a diameter before the tip of diagnostic extension 4120 that is thinner than the diameter of the tip of the diagnostic extension 4120. This thin diameter prior to the tip of the device may allow diagnostic extension 4120 more movement and better alignment with the canal and the tip with the eardrum. Diagnostic extension 4120 may include bulb 4125 with a diameter that allows for a predetermined distance (e.g., the radius of bulb 4125) to be maintained away from an ear canal wall. Bulb 4125 may include a video chip. Bulb 4125 may be rigid or flexible. Bulb 4125 may include a channel which may hold one or more wires to channel captured diagnostic data elsewhere or channel light to bulb 4125. Bulb 4125 may create a more benign distal end of the device, as opposed to a very small diameter which may exert more force or area and not deflect or bend off the ear canal wall as well as a tip with a rounded or radiused front outside edge. The shape of bulb 4125 may maintain a distance of light emitting or capturing elements from the wall of the canal (e.g., the distance is determined by the size of the bulb as elements are generally located away from the edges, as centrally as possible). Thus, the device may be better positioned to enable light to reach to and from the more distally located eardrum and the device and limit the percentage of light directed on the canal walls and absorbed or reflected back by the canal walls. The smaller diameter of diagnostic extension 4120 that exits the device enables the device to have a larger range of motion with the exit cavity of the device and within the ear canal. This larger range of motion enables the device to move further prior to bending. Less bending means a generally straighter extension which may be more likely to be in position to capture and image of the eardrum. Since the ear canal generally bends posterior at first and then anteriorly, a larger diameter device may bend more posteriorly. This may decrease the likelihood that an image of the more anteriorly located eardrum is captured. The ability for the diagnostic extension to move and float within the canal engagement as well as the smaller diameter extension, means less bending is required and less force against the canal walls. This may be important not only for alignment, but especially further into the canal where the canal walls are sensitive and can be easily injured.

Figure 42:
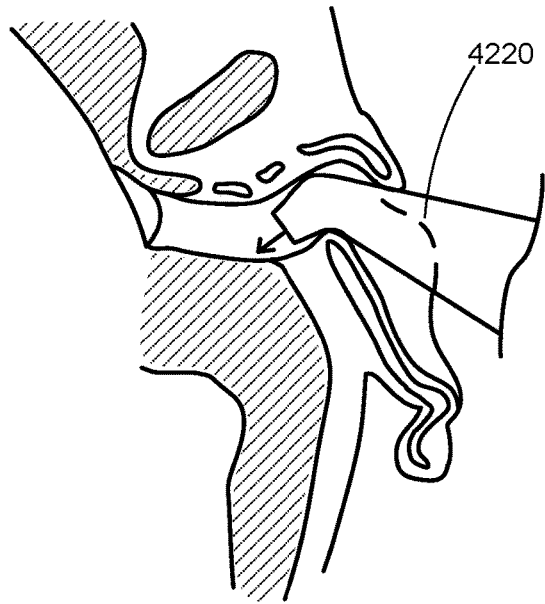
FIG. 42 depicts a flexible diagnostic extension having a tapered shape, in accordance with at least one embodiment.

FIG. 42 depicts a flexible diagnostic extension having a tapered shape, in accordance with at least one embodiment. Diagnostic extension 4220 may have a shape similar to a cone-shaped ear speculum. Diagnostic extension 4220 may be flexible and include diagnostic elements (e.g., an imaging chip) at the tip. Diagnostic extension 4220 having a typical or standard ear speculum shape may have a diameter that is closer to the size of the canal than a small diameter extension with a bulbous tip. Accordingly, the larger diameter may cause diagnostic extension 4220 to have less room to move within the canal. Further, the limited movement may be more restricted by contact at one or more points of the canal. Thus, the distal end of a flexible diagnostic extension 4220 may need to bend more to conform to the shape of the canal. As shown in FIG. 42, a portion of diagnostic extension 4220 bends backward (posteriorly) when in contact with the anterior wall of the ear canal. In some embodiments, this limited movement may result in a tip angle that is not in optimal alignment for capturing diagnostic information about the eardrum or that applies more force to the canal walls which may cause discomfort or cause an injury.

Figure 43:
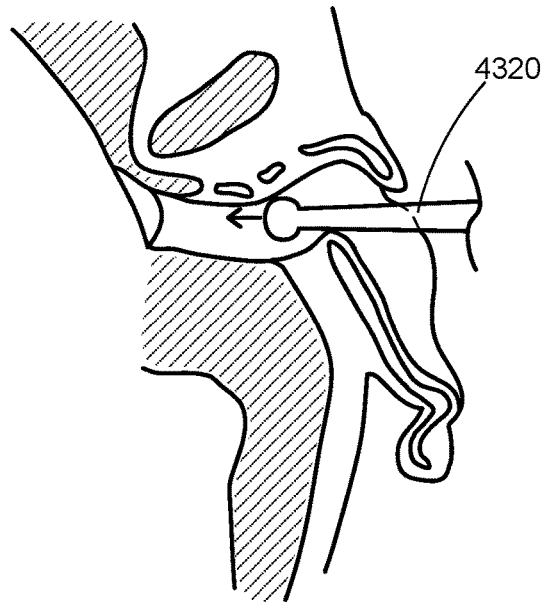
FIG. 43 depicts a diagnostic extension, in accordance with at least one embodiment.

FIG. 43 depicts a diagnostic extension, in accordance with at least one embodiment. Diagnostic extension 4320 may have a smaller diameter than the width of the ear canal and a smaller cross section than a typical speculum, at least in a segment proximal to the larger tip. This structure may allow more mobility of diagnostic extension 4320 within the ear canal (e.g., with minimal bending of diagnostic extension 4320). Further, this flexibility may enable diagnostic extension 4320 to navigate to a desired position for capturing diagnostic information from the eardrum. The extension may still be provided with a taper from proximal to distal similar to a speculum shape, with or without a larger bulb tip, but which has a smaller cross section, at least proximal to the tip, than typical/standard speculum sizes.

Figure 44:
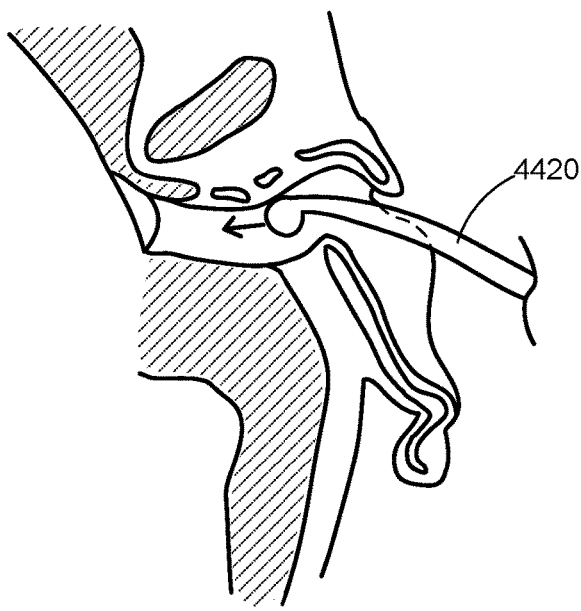
FIG. 44 depicts the diagnostic extension of FIG. 43 bending within an ear canal, in accordance with at least one embodiment.

FIG. 44 depicts the diagnostic extension of FIG. 43 bending within an ear canal, in accordance with at least one embodiment. The flexibility of diagnostic extension 4420 enables this bending. This bending may, in turn, change the direction at which the tip of diagnostic extension 4420 points. For example, diagnostic extension 4420 can move or bend in the canal prior to being restricted by multiple contact points with the canal wall, and the resulting shape of the bent diagnostic extension may cause the tip to be aligned towards the eardrum.

Figure 45:
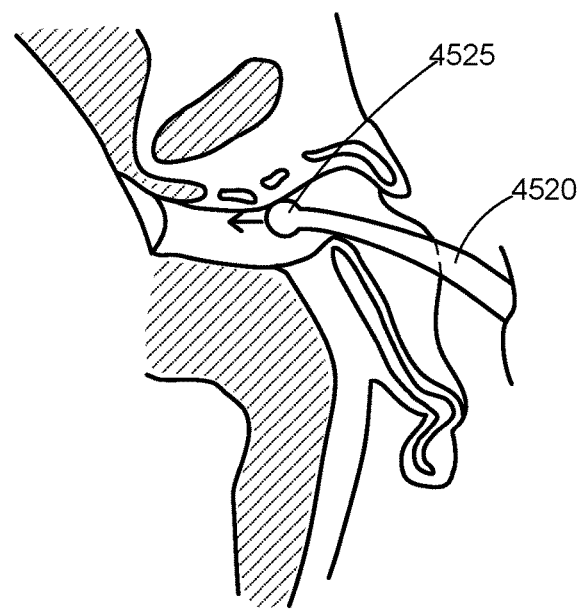
FIG. 45 depicts a diagnostic extension including a bulbous tip, in accordance with at least one embodiment.

FIG. 45 depicts a diagnostic extension including a bulbous tip, in accordance with at least one embodiment. In some embodiments, diagnostic extension 4520 includes bulb 4525, which may be a bulbous tip (e.g., having an oval or spherical shape with a larger diameter than the tube that comprises the majority of the length diagnostic extension 4520). The larger diameter of bulb 4525 can maintain a distance (e.g., the radius of bulb 4525) from the canal wall (e.g., to achieve a line of sight to the eardrum). Diagnostic extension 4520 can be constructed with varying flexibility. For example, diagnostic extension 4520 may be constructed so that flexibility increases from bulb 4525 towards the proximal end of the device. For example, diagnostic extension 4520 may include springs, each spring having a respective stiffness, where the stiffer springs are located near bulb 4525 and the more flexible springs are located near body 4515. This configuration may help diagnostic extension 4520 near bulb 4525 move in the ear canal prior to bending so that the angle is minimized and an ideal position and alignment with the eardrum is achieved. In some embodiments, diagnostic extension 4520 may be configured so that it is more flexible near bulb 4525 and less flexible near body 4515. This varying flexibility may also be provided by changing the pitch of the spring (e.g. a smaller pitch is more flexible) or by using a tapered or varying diameter wire to form the spring, where the wire is thicker in stiffer regions and thinner in regions where more flexibility is required.

Figure 46:
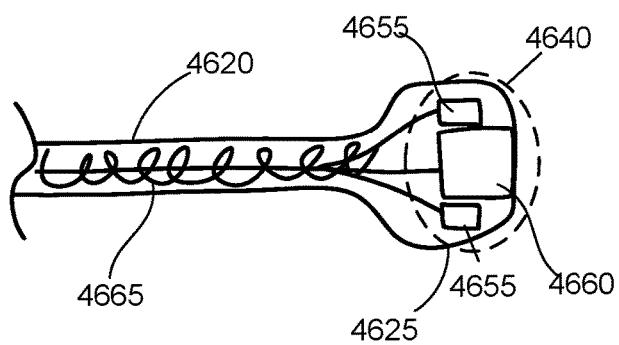
FIG. 46 depicts a diagnostic extension including a spring, in accordance with at least one embodiment.

FIG. 46 depicts a diagnostic extension including a spring, in accordance with at least one embodiment. Diagnostic extension 4620 may include a tube and bulb 4625. The diameter of the tube may be smaller than the diameter of bulb 4625. In some embodiments, the tube may be hollow (e.g., a tube with solid walls and a hollowed center to house wires to provide power or transmit data). Bulb 4625 may house diagnostic elements 4640. The diameter of bulb 4625 may help position diagnostic elements 4640 away from the canal wall (e.g., determined by the size of the bulb and in one example by a distance of ½ of the radius) and also allow sufficient room to house diagnostic elements such as LED(s), CMOS video chip and lens(es). Diagnostic elements 4640 may include one or more of a light source, imaging chip, communications circuitry, lenses, or any suitable component for obtaining diagnostic information (e.g., images, videos, temperature, pressure, etc.) of the ear canal or mouth. As shown in FIG. 46, diagnostic elements 4640 includes imaging chip 4660 and light sources 4655. Light sources 4655 may surround imaging chip 4660 on either side. Diagnostic extension 4620 may include spring 4665. Spring 4665 may provide flexibility to diagnostic extension 4620 and stiffness and elasticity to maintain the original shape of diagnostic extension 4620 (e.g., when counter forces of the ear canal are not applied to diagnostic extension 4620). For example, a representative flexibility and elasticity, with bending capability as illustrated in FIG. 41, comparable to a 2.5 mm extension with a spring with an ID of approximately 1.25 mm, pitch of approximately 2.5 mm, spring wire of 0.32-0.37 mm surrounding camera and LED wires and encapsulated with silicone. A stiffer or more flexible extension may be created by varying the wire diameter, pitch and extension/spring diameter. In some embodiments, the spring has a smaller diameter than 0.32 mm and the extension has a smaller diameter than 2.5 mm.

In some embodiments, additionally or alternatively, this characteristic may be achieved with plastics that do not take a set under force or are subjected to limited stresses that do not cause permanent shape change. Spring 4665 may include a straight wire, a coil, or a nitinol wire. Bulb 4625 may be constructed by molding around diagnostic elements 4640 or enclosing diagnostic elements 4640 in a preformed shell. The molding material or shell may be transparent or semi-transparent, allowing light to be emitted from within bulb 4625. This material may disperse the light so that it is more spread out with less local high intensity areas being created on tissue walls. Lenses can also be housed within bulb 4625 to diffuse the light. The distal end edges of bulb 4625 may be radiused and bulb 4625 may curve down from its maximum diameter or size to an edge that can be further radiused.

Figure 47:
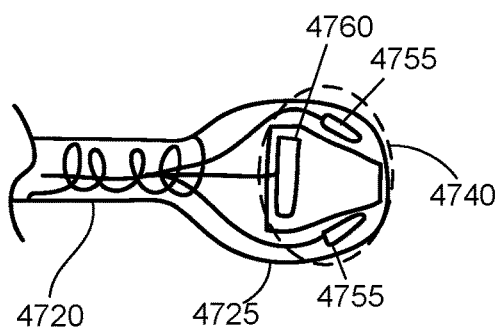
FIG. 47 depicts a diagnostic extension and a light input sized to enable positioning of light sources closer to the central axis of the diagnostic extension, in accordance with at least one embodiment.

FIG. 47 depicts a diagnostic extension and a light input sized to enable positioning of light sources closer to the central axis of the diagnostic extension, in accordance with at least one embodiment. Diagnostic extension 4720 may include a tube and bulb 4725, where the tube has a central axis which may run through the center of bulb 4725. Within bulb 4725 may be diagnostic elements 4740 which can include imaging chip 4760, light sources 4755, and a lens. The lens may be located at the tip of bulb 4725 and may capture light and transmit it to imaging chip 4760. The device configuration as shown in FIG. 46 or 47 may alternatively or additionally be used for measuring temperature. In some embodiments, the diagnostic device may include a source for infrared light, which may be used to determine thickness of a portion of the user's ear (e.g., tympanic membranes) or if there is fluid behind the eardrum. Compared to the configuration shown in FIG. 46, the configuration of the diagnostic device shown in FIG. 47 may have a configuration with a narrower light input (e.g., a smaller lens). This narrower light input may enable light sources 4755 to be located closer to the central axis of diagnostic extension 4720, potentially allowing for a smaller sized bulb 4725. In some embodiments, bulb 4625 or 4725 is semi-transparent or transparent to allow light sources 4655 or 4755, such as LEDs, to emit their light and be diffused for a more even lighting of the tissue walls. In some embodiments, a portion of bulb 4625 or 4725 is rigid, which may accommodate the rigid video chip and lens configuration.

Diagnostic extension may have a height or diameter less than 5 millimeters. For example, a diameter of 2 millimeters or less may enable the most ease for positioning in various anatomy and canal shapes. In another example, diagnostic extension 4620 or 4720 may be configured with a diameter of 1 millimeter or smaller. In some embodiments, diagnostic extension 4620 or 4720 having a diameter closer to 5 millimeters may not require a bulb (e.g., bulb 4625 or 4725) having a diameter that is even larger. For example, a 4 or 5 millimeter diameter of diagnostic extension 4620 or 4720 may be large enough to maintain sufficient distance from the canal wall and be sufficient size to house diagnostic components. It is preferred, but not necessary, that smaller sized diagnostic extensions, such as those having diameters of 1-2 millimeters, have a slightly larger sized bulb. The bulb may have diameters from 1-5 millimeters, although it is possible for larger or smaller diameters. Diameter of the bulb may preferably be between 2.5-4.0 millimeters to house diagnostic components and maintain a sufficient distance of the diagnostic components from the canal wall.

Figure 48:
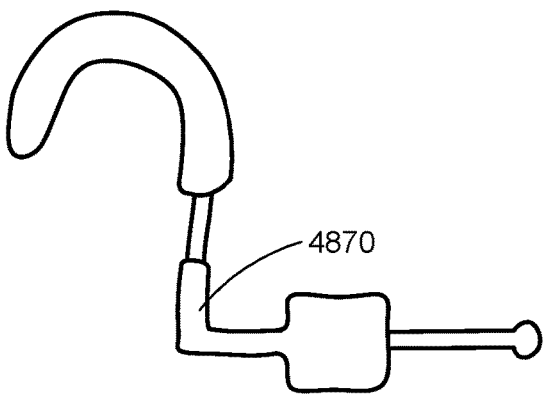
FIG. 48 depicts a diagnostic device in a bent position, in accordance with at least one embodiment.

FIG. 48 depicts a diagnostic device in a neutral position with a bend, in accordance with at least one embodiment. A diagnostic device may include two portions (e.g., a first more vertical segment and a second more horizontal segment) connected by flexible joint 4870. Alternatively or additionally, the device may include a hinge that connects the two portions. Flexible joint 4870 allows the device to be straightened or bent. For example, the device may be straightened out to fit into an attachment to capture diagnostic information (e.g., images) of the mouth and throat.

Figure 49:
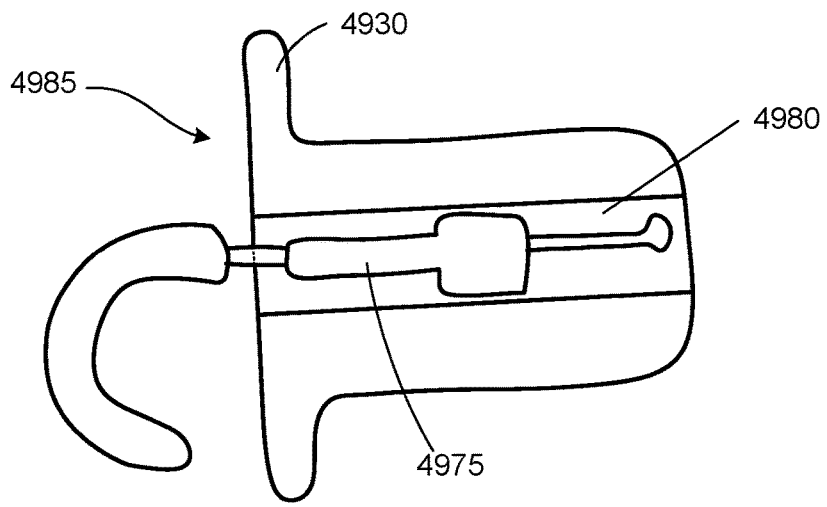
FIG. 49 depicts the diagnostic device of FIG. 48 in a straightened position and having an oral attachment placed onto the device, in accordance with at least one embodiment.

FIG. 49 depicts the diagnostic device of FIG. 48 in a straightened position and having an oral attachment placed onto the device, in accordance with at least one embodiment. The device of FIG. 48 may be rotated about joint 4870 (i.e., straightened joint 4975) to obtain the straightened configuration shown in FIG. 49. The device may be inserted into attachment 4985 so diagnostic elements are located near or at the tip of the oral attachment. Attachment 4985 may include stop 4930, channel 4980 to fit the device. In some embodiments, attachment 4985 or the diagnostic device of FIG. 48 includes an attachment means (e.g., a snap fit or press fit via compressible surface cavities or protrusions that couple to one another) to enable the device and attachment to couple to one another. In a straightened position, the diagnostic device of FIG. 48 (e.g., a diagnostic device capable of obtaining diagnostic information about the ear) can be inserted further into attachment 85 and the diagnostic extension with diagnostic elements at or near the tip of the extension may reach further into attachment 4985. Attachment 4985 includes stop 4930 to prevent over insertion into the mouth. In some embodiments, although not depicted, attachment 4985 may include a handle to hold attachment 4985. As depicted in FIG. 49, the over ear piece of the diagnostic device of FIG. 49 may serve as a handle. In some embodiments, a diagnostic kit may include the device of FIG. 49 and various sizes of attachment 4985 to fit different sized mouths.

Figure 50A:
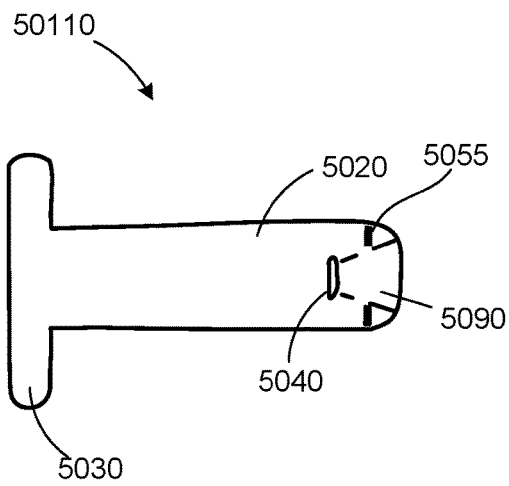
FIGS. 50A-B depict side and top views of an oral and diagnostic device having a tapered opening, in accordance with at least one embodiment.
Figure 50B:
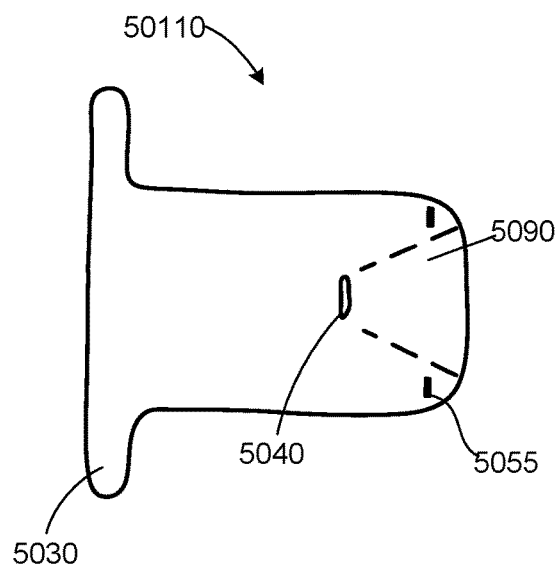
Figure 51:
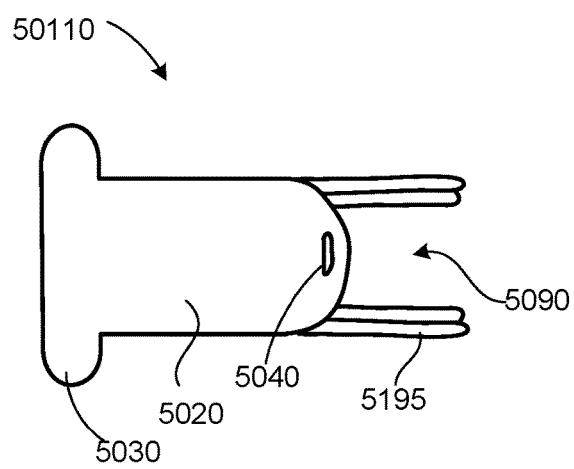
FIGS. 51-52 depict the device of FIGS. 50A-B having distal extensions, in accordance with at least one embodiment.
Figure 52:
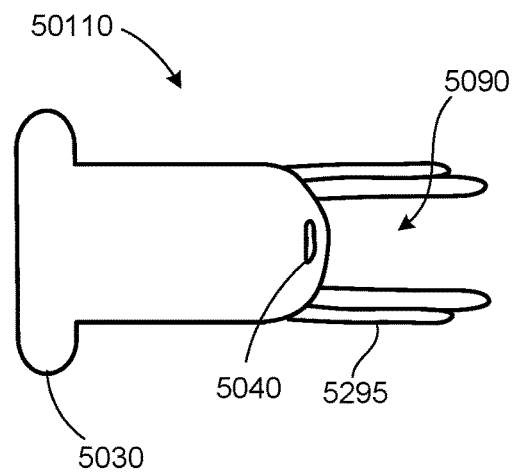

FIGS. 50A-B depict an oral and diagnostic device having tapered openings, in accordance with at least one embodiment. FIGS. 51-52 depict the device of FIGS. 50A-B having distal extensions, in accordance with at least one embodiment. FIG. 50A depicts a side view (i.e., looking in a medial-lateral direction if oral and diagnostic device 50110 was in a user's mouth) of oral and diagnostic device 110 for viewing the mouth or throat. FIG. 50B depicts a top view (i.e., looking in a superior-inferior direction if oral and diagnostic device 50110 was in the mouth) of oral and diagnostic device 50110. Oral and diagnostic device 50110 of FIGS. 50A and 50B may include stop 5030, diagnostic elements 5040, light sources 5055, and diagnostic window 5090. Diagnostic window 5090 may include a tapered cavity and an opening. Diagnostic window 5090 may taper such that the window widens away from diagnostic element 5040 and towards the distal end of oral and diagnostic device 50110. Diagnostic window 5090 may provide distance between the end of oral and diagnostic device 50110 and diagnostic element 5040 and an opening of a sufficient height (e.g., 50-80% of the height of oral and diagnostic device 50110) to channel the diagnostic information from the end of oral and diagnostic device 50110 to diagnostic element 5040. In some embodiments, the opening and the cavity are sufficiently large for the field of view of an imaging chip. The cavity can be open and exposed to the surrounding environment or it can be covered with a transparent end (e.g., a clear plastic). The covering for the cavity vary depending on the diagnostic information that is being captured. For example, if sound is being captured, a diaphragm type covering may not be visibly transparent, but it may be able to transmit sound. In the configuration shown, light sources 5055 are located near the end of oral and diagnostic device 50110. In some embodiments, light is prevented from traveling from light sources 5055 directly back to diagnostic element 5040 or from reflecting off oral and diagnostic device 50110 directly from light sources 5055 and traveling back to diagnostic element 5040. In some embodiments, light is directed out from oral and diagnostic device 50110 towards the diagnostic area of interest, from where it is reflected back into the cavity of oral and diagnostic device 50110 and to diagnostic element 5040. Again, other diagnostic information may be captured (e.g., sound). In some embodiments, oral and diagnostic device 50110 may include speakers. Sound waves may be emitted by speakers near the end of oral and diagnostic device 50110, and sound waves reflected from the diagnostic area of interest may be captured by diagnostic element 5040. In some embodiments, oral and diagnostic device 50110 is an attachment without a dedicated power source. This attachment may include electrical contacts to connect to electrical contacts in a device having a dedicated power source. FIGS. 51 and 52 show oral and diagnostic device 50110 of FIGS. 50A and 50B having distal extensions 5195 and 5295, respectively, coupled to the surface of oral and diagnostic device 50110. Distal extensions 5195 and 5295 may be coupled to the tip of oral and diagnostic device 50110.

Figure 53:
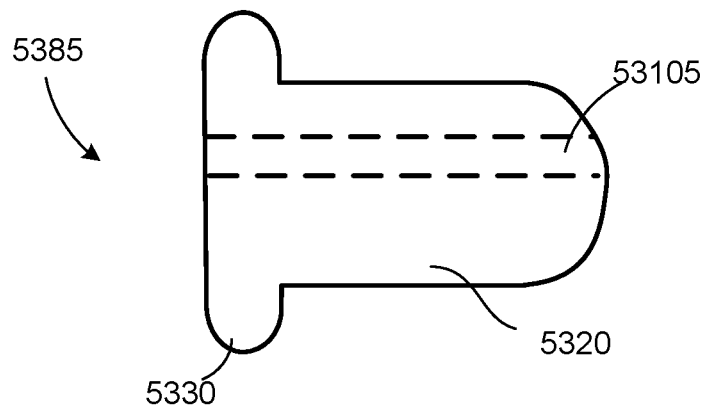
FIGS. 53-55 depict various configurations of channels through which diagnostic information is captured through oral attachments, in accordance with at least one embodiment.
Figure 54:
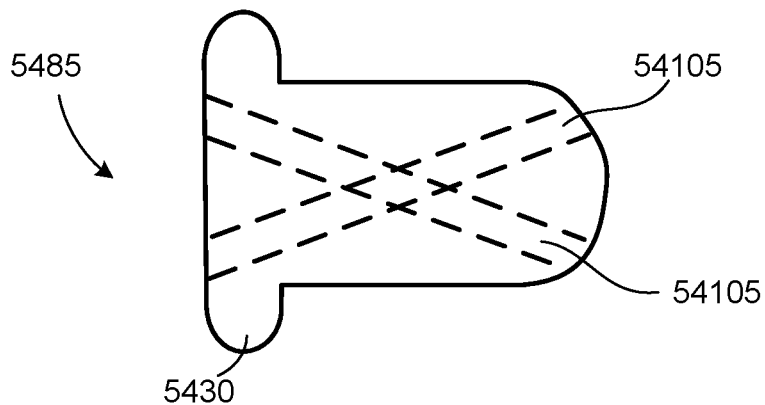
Figure 55:
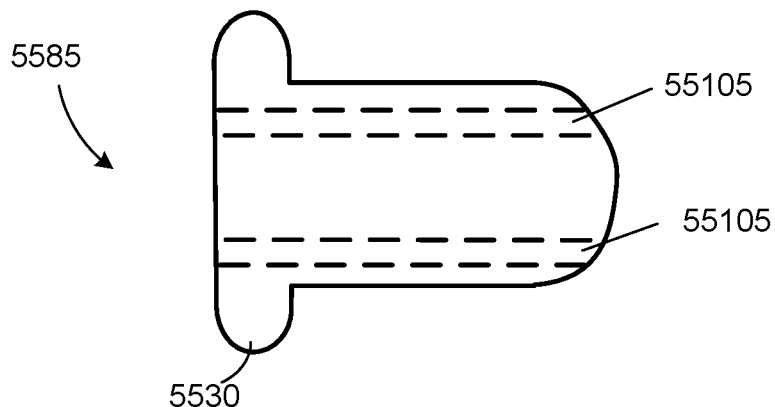

FIGS. 53-55 depict various configurations of channels through which diagnostic information is captured through oral attachments, in accordance with at least one embodiment. Attachments 5385, 5485, and 5585 may include one or more channels (e.g., channels 53105, 54105, and 55105) through which a diagnostic device may be inserted. For example, a swab may be inserted through channel 53105 and out the end, in a direction towards a tonsil, to contact the tonsil and capture biological fluids. The attachment may be configured to interface with the tongue and mouth to align channels with a tonsil. Attachments 5385, 5485, and 5585 may be placed in the mouth so that the channels generally align with the diagnostic area of interest. A tonsil or a swab may be passed through channel 55105, near to or out of the end of attachment 5585. Various other attachments can be configured with channels to capture diagnostic information from other body parts. For example, a device or attachment configured to capture diagnostic information within a nasal cavity may have a cavity through which diagnostic tools may be inserted and passed through. FIG. 53 depicts is a side view of attachment 5385 showing channel 53105 running through attachment 5385. FIG. 54 depicts a top view of attachment 5485 having two channels 54105 running and overlapping through attachment 5485. The configuration shown in FIG. 54 may allow a diagnostic tool to reach a position further to the side or a more lateral position within a mouth. FIG. 55 depicts a top view of attachment 5585 having two channels 55105 running in parallel with one another through attachment 5585.

Figure 56A:
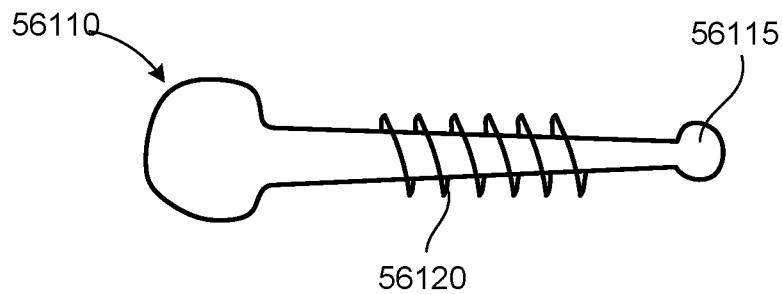
FIGS. 56A-B depict an oral and diagnostic device and the device within an oral attachment, respectively, in accordance with at least one embodiment.
Figure 56B:
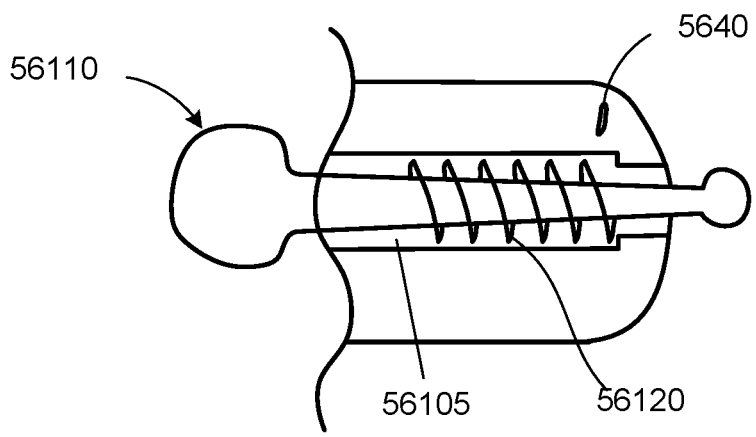

FIGS. 56A-B depict an oral and diagnostic device and the device within an oral attachment, respectively, in accordance with at least one embodiment. Oral and diagnostic device 56110 may include spring 56120 and swab tip 56115. FIG. 56A shows an example of oral and diagnostic device 56110. FIG. 56B shows an example of oral and diagnostic device 56110 inserted into an attachment. Oral and diagnostic device 56110 may be inserted through channel 56105 in an attachment to capture diagnostic information. Swab tip 56115 may collect biological fluids from the throat or tonsil area. Swab tip 56115 may be absorbent. Spring 56120 may be attached to oral and diagnostic device 56110 at the end of the device closer to the handle and away from swag tip 56115 that collects diagnostic data. In some embodiments, the distal end of oral and diagnostic device 56110 is free floating within an attachment. A user may engage with spring 56120 may applying force to oral and diagnostic device 56110 and causing swab tip 56115 to extend as spring 56120 compresses. A stop or certain length of spring 56120 can be constructed to limit length that can exit the end of the device. For example, spring 56120 may be 30% of the length of the attachment or 50% of the length of oral and diagnostic device 56110. In some embodiments, spring 56120 may be coupled to the attachment (i.e., the spring is coupled to the attachment rather than oral and diagnostic device 56110). Oral and diagnostic device 56110 may be constructed with a retractable or compressible spring section, so that swap tip 56115 retracts into the attachment when it encounters force. This may limit the amount of force that can be applied to a diagnostic area of interest to prevent damaging tissue or causing pain to the user. In some embodiments, diagnostic elements 5640 may be included within the attachment through which oral and diagnostic device 56110 fits.

Figure 57:
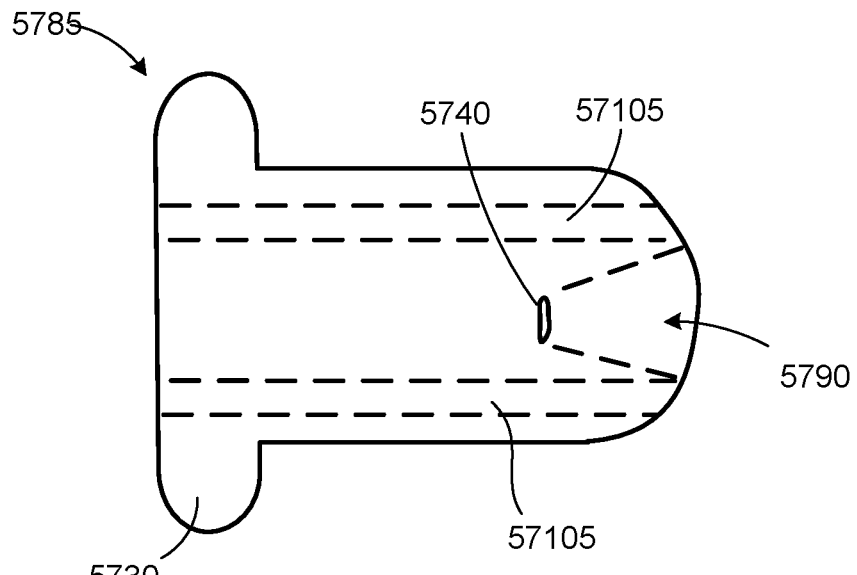
FIG. 57 depicts an oral attachment having a tapered opening and diagnostic channels, in accordance with at least one embodiment.

FIG. 57 depicts an oral attachment having a tapered opening and diagnostic channels, in accordance with at least one embodiment. Oral attachment 5785 may include stop 5730, channels 57105 for a diagnostic tool to pass through, diagnostic window 5790, and diagnostic element 5740. Diagnostic window 5790 may be a large opening (e.g., a height of 50-80% of the height of attachment 5785. In some embodiments, oral attachment 5785 may be an oral device. Oral attachment 5785 may be configured similar to the device depicted in FIG. 50A-B to obtain diagnostic information. Channels 57105 may have a height or width greater than the height and width of oral and diagnostic device 57110 to enable oral and diagnostic device 57110 to pass through channel 57105 (e.g., similar to FIGS. 53-55 and 56A-B)

Figure 58:
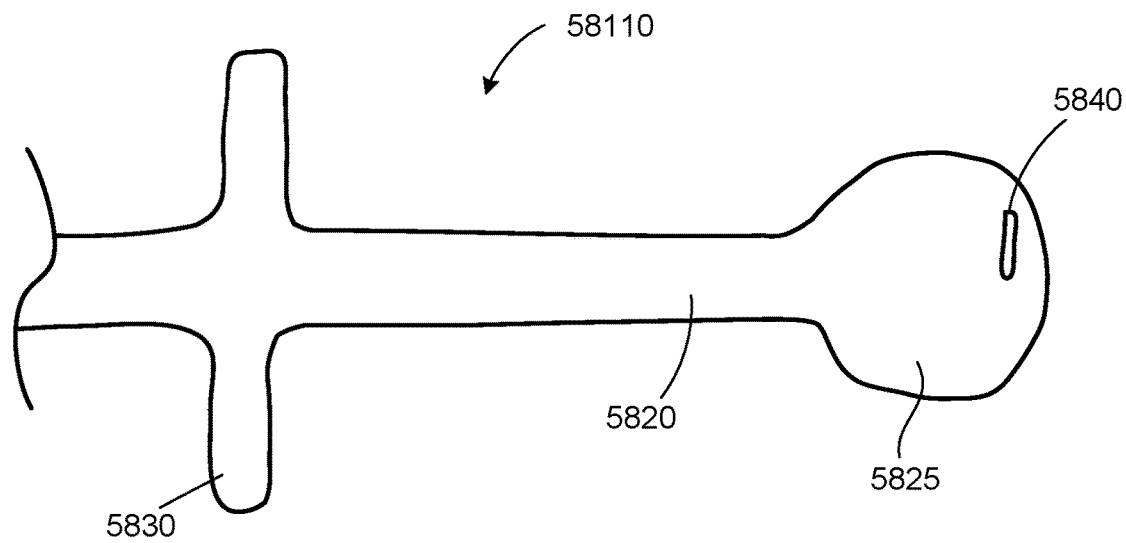
FIGS. 58-59 depict diagnostic devices for capturing diagnostic information about a mouth or throat, in accordance with at least one embodiment.
Figure 59:
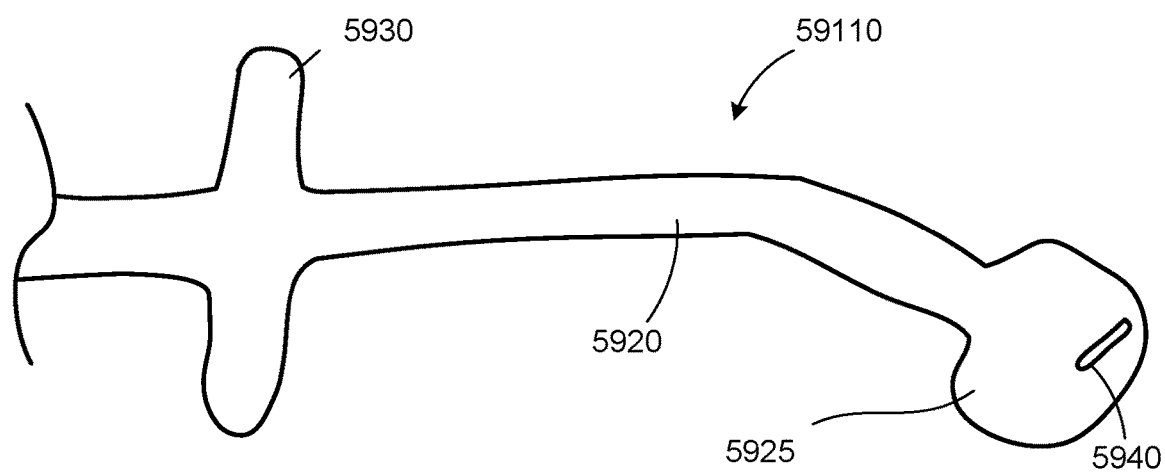

FIGS. 58-59 depict diagnostic devices for capturing diagnostic information about a mouth or throat, in accordance with at least one embodiment. Oral and diagnostic device 58110 may include stop 5830, diagnostic extension 5820, bulb 5825, and diagnostic elements 5840. Oral and diagnostic device 59110 may include stop 5930, diagnostic extension 5920, bulb 5925, and diagnostic elements 5940. Oral and diagnostic device 58110 or 59110 may have a height and width allowing it to fit through a channel of an attachment, as described with reference to FIGS. 49, 53-55, and 56B. Examples of various oral and diagnostic devices are further described in U.S. patent application Ser. No. 15/920,208, filed on Mar. 13, 2018, and U.S. patent application Ser. No. 15/573,432, filed on May 12, 2016, each of which is hereby incorporated by reference in their entireties. FIG. 58 shows one example of oral and diagnostic device 58110 with bulb 5825 at the distal end of the device having a diameter larger than the diameter of diagnostic extension 5820. This larger diameter may allow for adequate space between regions of the mouth or throat contacted by oral and diagnostic device 58110 and the diagnostic elements 5840 housed within bulb 5825. FIG. 59 shows bulb 5925 of oral and diagnostic device 59110 angled downward, or inferiorly when inserted into the mouth. Accordingly, diagnostic elements 5940 are also angled downward. Oral and diagnostic device 59110 may be constructed with a concave inferior or bottom, which may help oral and diagnostic device 59110 align with anatomy or depress tissue to align with the throat. Oral and diagnostic device 58110 or 59110 may also be constructed with a convex top, or superior side, which may help oral and diagnostic device 58110 or 59110 conform to the palate or roof of the mouth, as well as the soft palate. Oral and diagnostic device 58110 or 59110 may have a convex surface on the top and concave surface on the bottom. Oral and diagnostic device 58110 or 59110 may be configured with a larger section near the distal end of oral and diagnostic device 58110 or 59110 that is furthest inserted into the mouth towards the throat to push tissue away and create an opening in front of the end of oral and diagnostic device 58110 or 59110 to capture diagnostic information. Diagnostic elements 5840 or 5940 (e.g., imaging elements) may located in a top region of the bulb of oral and diagnostic devices.

Figure 60:
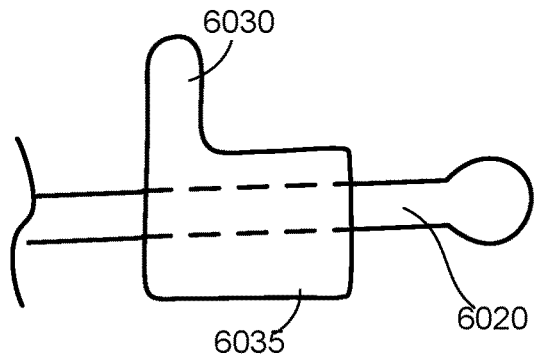
FIGS. 60-63 depict wand type devices, in accordance with at least one embodiment.
Figure 61:
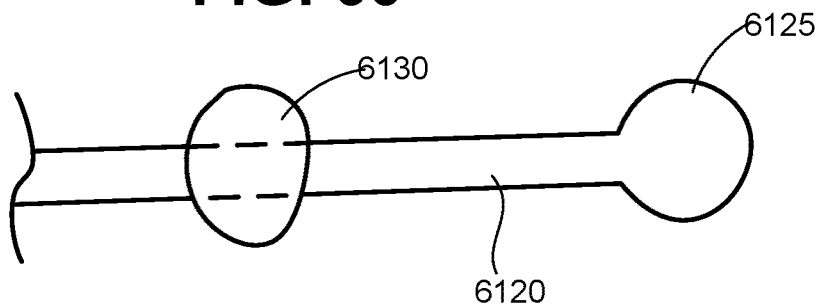
Figure 62:
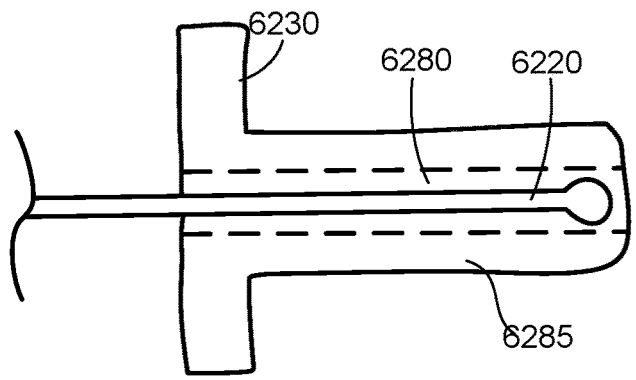
Figure 63:
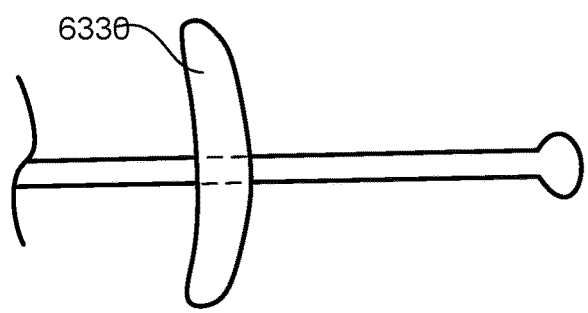

FIGS. 60-61 depict wand type devices, in accordance with at least one embodiment. FIG. 60 is a wand type device including diagnostic extension 6020 and coupled to an attachment having stop 6030 and ear canal engagement section 6035. FIG. 61 is a wand type device including diagnostic extension 6120 and coupled to an attachment having stop 6140 and bulb 6125. FIG. 62 is a wand type device including diagnostic extension 6220 and coupled to attachment 6285 having stop 6230, channel 6280. FIG. 63 is a wand type device coupled to an attachment having stop 6330. The device has a distal end that may be sized to fit into the ear canal (e.g., preferably no larger than a standard ear speculum). The distal end may be at least an inch long, although it could be shorter. In some embodiments, the distal end is 2 inches or longer. For example, diagnostic extension 6020 may be 1.5 inches long. It is preferred that this distal end of the device has a small diameter or size section leading up to a larger size or diameter tip. The distal end of the device and the larger size tip may be configured according to FIGS. 41-47 and the corresponding specification describing the figures. The proximal end of the device can be connected to a handle or continue for a long length and be flexible with a connection to a control box. The handle or control box can contain the electronics of the device. The combination of the device connected to control box or the device having a handle may both be examples of a standalone device which can capture diagnostic information. This standalone device may emit or capture light. In some embodiments, a kit may include a wand type device and attachments. For example, an attachment for imaging the ear may include stop 6030 and ear canal engagement section 6035. Another example is oral attachment 6285 which the device fits into (e.g., via channel 6280). Oral attachment 6285 fits into the mouth and helps align the tip of the device with the mouth. The device may include attachments such as a safety mechanism (e.g., stop 6330 of FIG. 63) of sufficient size that prevents over-insertion into the ear canal by being large enough in size that it cannot enter the ear canal. This safety mechanism can be flexible enough that it bends to fit into attachments (e.g., attachment 6285). In some embodiments, diagnostic extensions may be inserted into a device similar in configuration to the device of FIG. 1. The device of FIG. 1 may have an opening for the distal end of device to be inserted through the back of the device and extend out into the ear canal similar to diagnostic extension 120 in FIG. 1. For example, the wand type device may be connected to the device of FIG. 1 through a snap fit mechanism, magnetic mechanism, or any suitable mechanism for attaching the device within a channel of the device.

Figure 64A:
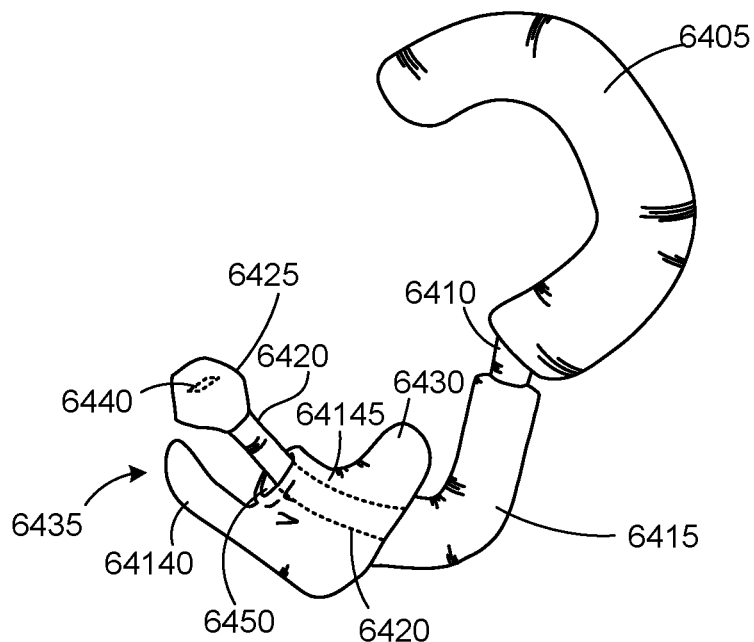
FIGS. 64A-D depict a diagnostic device having a stop configured to contact an area superior to the ear canal entrance and an ear canal engagement configured to contact the inferior ear canal wall, in accordance with at least one embodiment.
Figure 64B:
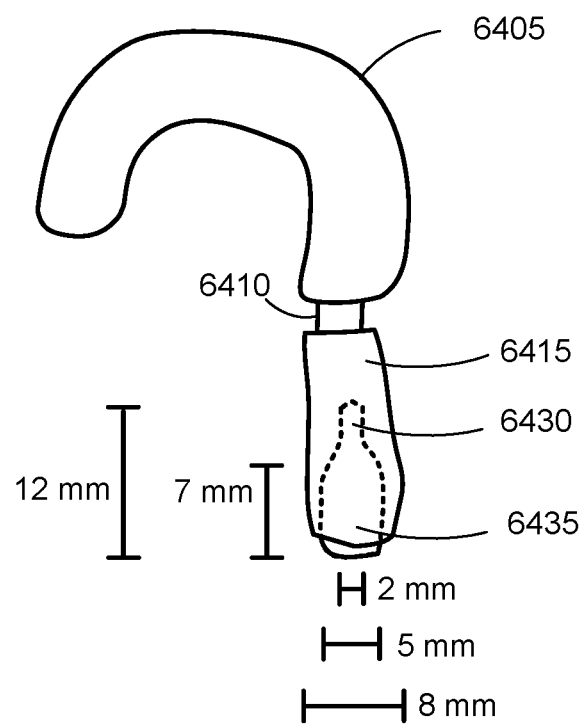
Figure 64C:
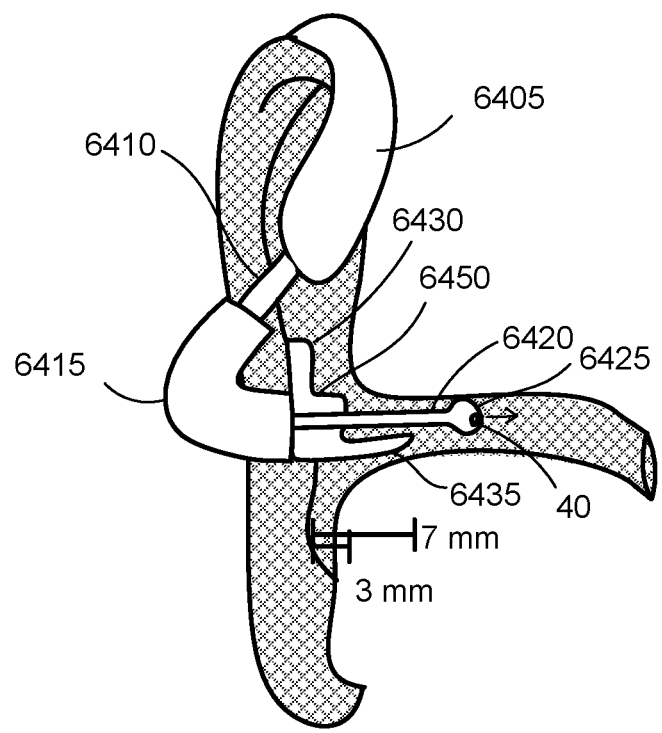
Figure 64D:
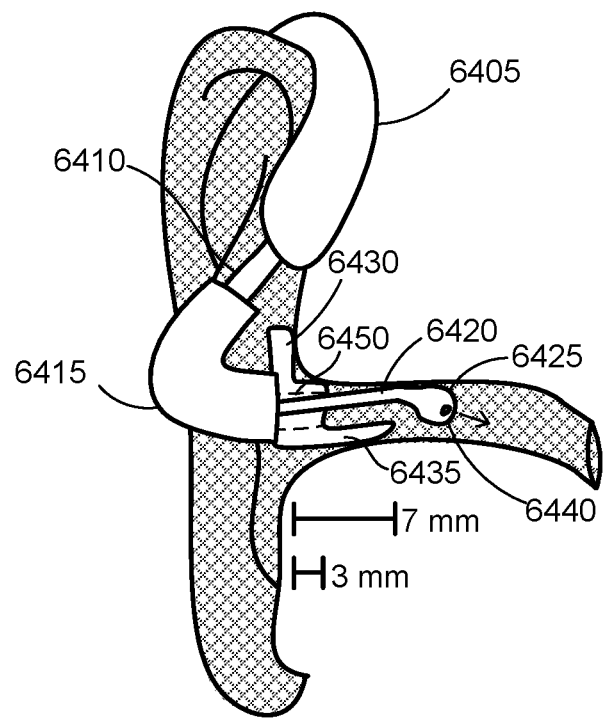

FIGS. 64A-D depict a diagnostic device having a stop configured to contact an area superior to the ear canal entrance and an ear canal engagement configured to contact the inferior ear canal wall, in accordance with at least one embodiment. In another embodiment, the ear canal engagement section is also configured to contact a superior wall. FIGS. 64C-D include measurements purely for illustration and variations in the measurements will be recognized within those skilled in the art as falling within scope of this description. FIG. 64A depicts an isometric view of the diagnostic device. FIG. 64B depicts a rear view of the diagnostic device. FIG. 64C depicts the diagnostic device partially inserted into an ear canal. FIG. 64D depicts the diagnostic device inserted into the ear canal.

The diagnostic device includes over ear piece 6405, post 6410, body 6415, diagnostic extension 6420, bulb 6425, ear canal engagement section 6435, diagnostic elements 6440, and channel 6450 for diagnostic extension 6420. Over ear piece 6405 may be coupled to body 6415 via post 6410 as described with respect to FIG. 1. The diagnostic device may be wireless (i.e., no wires exit from the device and connect to an external device) and include communications circuitry to communicate diagnostic information collected by diagnostic elements 6440. For example, communications circuitry may be located within body 6415 and a wire extending from body 6415 to bulb 6425 (e.g., through ear canal engagement section 6435 and diagnostic extension 20) may provide captured diagnostic information to the communications circuitry for transmission to an external device. Body 6415 may include ear canal engagement section 6435.

Ear canal engagement section 6435 and body 6415 may be permanently attached (e.g., assembled as one piece) or removable from one another (e.g., via a snap fit mechanism between the external surface of body 6415 and the internal surface of ear canal engagement section 6435). Ear canal engagement section 6435 may include upper portion 64145 and sled 64140. Upper portion 64145 is a portion of canal engagement section 6435 configured to contact the inferior wall of the ear. For example, upper portion 64145 may be located on a side of ear canal engagement section 6435 that is closest to over ear portion 6405. Stop 6430 is coupled to ear canal engagement section 6435 to prevent over insertion of the diagnostic extension 6420 or ear canal engagement section 6435. Stop 6430 may have a width that is smaller than its height (e.g., as shown in FIGS. 64B and 65C).

Body 6415 may include a first portion and second portion. The first portion of body 15 include ear canal engagement section 6435, channel 6450, and a channel opening for channel 6450. The length of the first portion of body 6415, a length of channel 6450, and a length of ear canal engagement section 6435 may extend along a first axis. A height of the first portion of body 6415 may extend along a second axis that is orthogonal to the first axis. A width of the first portion of body 6415 may extend along a third axis that is orthogonal to both the first and second axes. The width of the first portion of body 6415 may be smaller than its height. A first portion of ear canal engagement section 6435 may extend farther along the first axis than a second portion of ear canal engagement section 6435. For example, in FIGS. 64C and 64D, the first, inferior, portion is 7 millimeters long and the second, superior, portion is 3 millimeters long. A surface of the first portion of ear canal engagement 6435 may curve towards the second portion of ear canal engagement section 6435. For example, as shown in FIGS. 64C and 64D, the bottom surface of ear canal engagement section that contacts the inferior wall of the ear canal curves upward towards diagnostic extension 6420 or the upper half of ear canal engagement section 6435. In another embodiment the bottom surface of the first portion is configured flat and the bottom of the front of (most distal tip) the first portion may be radiused to aid in insertion and reduce likelihood for injury or discomfort. The second portion of body 6415 may be coupled to post 6410, which is further coupled to over ear piece 6405. In some embodiments, the first and second portions may be connected to one another by a hinge.

Diagnostic extension 6420 may be coupled to body 6415. Diagnostic extension 20 may be made from a flexible material (e.g., silicone). With reference to the previous first, second, and third axes, diagnostic extension 6420 may extend along the first axis. In some embodiments, diagnostic extension 6420 is substantially parallel to the first portion of ear canal engagement section 6435. Diagnostic extension 6420 may include bulb 6425 at its distal end. Bulb 6425 may house one or more diagnostic elements 6440, which may include a light source, imaging chip or circuitry, or a camera. Diagnostic extension 6420 may further include a tube coupled to bulb 6425, where the tube exits body 6415 through ear canal engagement section 6435 (e.g., the second portion) at the channel opening of channel 6450. In another embodiment, diagnostic extension 6420 is solid, with plastic or rubber fully encapsulating internal components such as camera and LED wires and spring. Channel 6450 is within ear canal engagement section 6435 and is wider or taller than diagnostic extension 6420's width or height, respectively, to allow more space for diagnostic extension 6420 to move side-to-side or up-and-down or at an angle. Channel 6450 may thus allow diagnostic extension 6420 or bulb 6425 to be more mobile when contacting walls of the ear canal prior to flexing or bending, which further increases the likelihood that diagnostic element 6440 may be positioned with the object of diagnosis accessible. For example, diagnostic element 6440 may include an imaging chip and the channel 6450 provides diagnostic extension 6420 more space to move in response to contact with a superior wall of the ear canal, and the imaging chip within bulb 6425 may have better access to capture images of the eardrum after diagnostic extension 6420 has moved within the space provided by channel 6450.

FIG. 64B indicates dimensions of body 6415, ear canal engagement section 6435, and stop 6430 of the diagnostic device. In some embodiments, stop 6430 may have a width that is narrower than an ear canal width, which may be 4-10 millimeters wide. For example, stop 6430 may have a width of 2 millimeters. In some embodiments, ear canal engagement section 6435 may have dimensions (e.g., a maximum width or height of the portion inserted into the canal that excludes stop 6430) that is substantially equivalent to the dimensions of the ear canal. For example, ear canal engagement section 6435 may have a width of 5 millimeters and a height of 7 millimeters. Body 6415 may be coupled to ear canal engagement section 6435 such that the bottom of ear canal engagement section 6435 is lower or the same level as the bottom of body 6415. As depicted in FIG. 64B, the bottom of ear canal engagement section 6435 is lower than the bottom of body 6415.

FIGS. 64C and 64D show examples of the diagnostic device with diagnostic extension 6420 straightened and bent, respectively. The anatomy of the ear is depicted using hatch marks to differentiate it from the diagnostic device. Bulb 6425 is angled downwards within the ear canal, as depicted in FIG. 64D, due to the contact between the smaller diameter section of the diagnostic extension proximal to bulb 6425 (e.g., a tube) or bulb 6425 against the superior wall of the ear canal. FIGS. 64C and 64D include arrows pointing from diagnostic element 6440 in the direction in which, for example, a camera may capture diagnostic information (e.g., an image). When the device is partially inserted in FIG. 64C, diagnostic extension 6420 may be straight in a neutral position and diagnostic element 6440 is at a neutral position (e.g., unaffected by forces from contact with the ear canal) and may point straight ahead. In FIG. 64C, diagnostic element 6440 may be pointed towards the ear canal wall. By comparison, in FIG. 64D, diagnostic element 6440 is pointed downwards towards the eardrum due to contact between diagnostic extension 6420 or bulb 6425 and the superior ear canal wall.

Figure 65A:
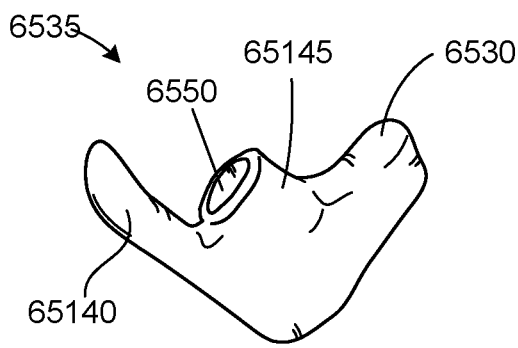
FIG. 65A-D depict an ear canal engagement section having a sled, in accordance with at least one embodiment.
Figure 65B:
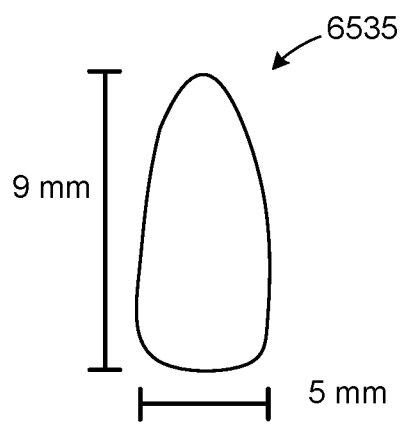
Figure 65C:
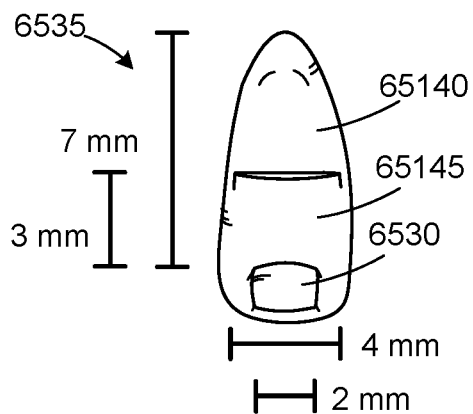
Figure 65D:
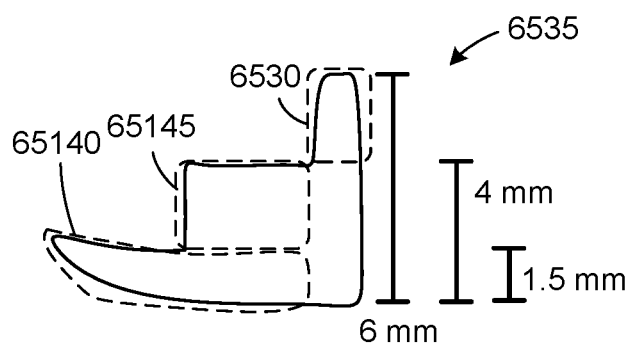

FIGS. 65A-D depict an ear canal engagement section having a sled, in accordance with at least one embodiment. Ear canal engagement section 6535 of FIGS. 65A-D may serve as or be equivalent to ear canal engagement section 6435. FIGS. 65A-D include measurements purely for illustration and variations in the measurements will be recognized within those skilled in the art as falling within scope of this description. FIGS. 65A-D depict various views of ear canal engagement section 65: FIG. 65A depicts an isometric view, FIG. 65B depicts a bottom view, FIG. 65C depicts a top view, FIG. 65D depicts a side view. Ear canal engagement section 6535 may include stop 6530, channel 6550 through which a diagnostic extension may exit, sled 65140, and upper portion 65145. Although not shown, ear canal engagement section 6535 may be coupled to body 6515. The length of ear canal engagement section 6535 may vary depending upon the size of the ear (e.g., infants under approximately 1 year of age have shorter ear canals than adults). The length may be approximately a third of the length of the ear canal for which it is intended to be used. For example, for an adult ear having a length of approximately 25 millimeters, the length may be 8-10 millimeters. The example measurement depicted in FIG. 65B is 9 millimeters. The width of ear canal engagement section 6535 may be substantially equivalent to the width of the ear canal. The example measurement depicted in FIG. 65B is 5 millimeters. Upper portion 65145 may have a width that is equivalent or less than the width of the ear canal and greater than the width of the diagnostic extension. The example measurement of the width of upper portion 65145 in FIG. 65C is 4 millimeters. The width of stop 6530 may be narrower than the ear canal width. The example measurement of the width of stop 6530 is 2 millimeters.

Sled 65140 may be adapted such that ear canal engagement section 6535 angles upward when the sled 65140 contacts an inferior wall of the ear canal. For example, the length of sled 65140 may be longer than the length of upper portion 65145 to angle section 6535 upward when sled 65140 contacts the inferior wall of the ear canal. The length of sled 65140 may be measured from stop 6530 to the tip of sled 65140 at the distal end of ear canal engagement section 6535. An example length of sled 65140 is 7 millimeters. The length of upper portion 65145 may be measured from stop 6530 to the opening of channel 6550 or if extending past the opening, from stop 6530 to the tip of upper portion 65145 at the distal end of ear canal engagement section 6535. An example length of upper section 65145 is 3 millimeters. An example height of ear canal engagement section 6535 is 6 millimeters, where stop 6530 may be approximately 25-35% the height of ear canal engagement section 6535. For example, stop 6530 extends 2 millimeters past the height of upper portion 65145 as depicted in FIG. 65D. In another example, stop 6530 extends 6 millimeters past the height of upper section 65145. Sled 65140 may vary in height along its length. Sled 65140 may curve upwards. The height of sled 65140 may be largest closest to the proximal end of ear canal engagement section. In one example, the maximum height of sled 65140 is 1.5 millimeters.

Figure 66:
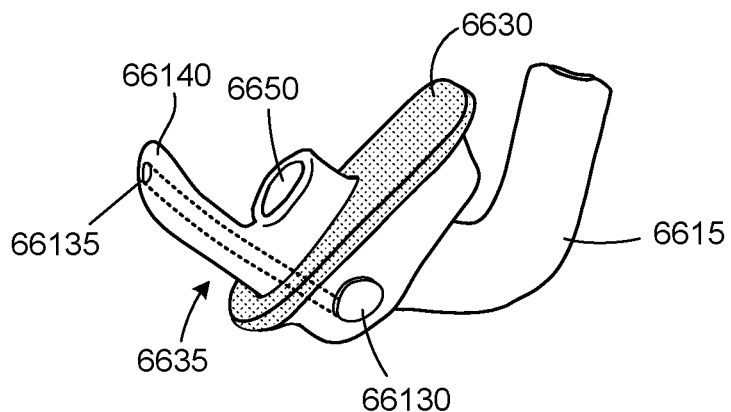
FIG. 66 depicts a portion of a diagnostic device including an air injection button and air outlet port, in accordance with at least one embodiment.

FIG. 66 depicts a portion of a diagnostic device including an air injection button and air outlet port, in accordance with at least one embodiment. In some embodiments, a diagnostic device for the ear includes a means to pressurize the ear canal. The diagnostic device may include body 6615, which includes ear canal engagement section 6635. Ear canal engagement section 6635 includes stop 6630, channel 6650, sled 66140, air injection button 66130, and air outlet port 66135. In some embodiments, air outlet port 66135 is located at the distal end of ear canal engagement section 6635. For example, air outlet port 66135 is located at an inferior position (e.g., exiting from the external surface of sled 66140) of sled 66140. Air outlet port 66135 may be connected to air ports in body 6615 of the diagnostic device that may be pressurized by depressing one or more buttons 66130, sending air out air outlet port 66135 and pressurizing the ear canal. In some embodiments, air outlet port 66135 is connected via tubing to an external box which houses one or more air injection buttons 66130 that may be depressed or squeezed to send air through the tubing and out through air outlet port 66135 to pressurize the ear canal. In some embodiments, a flexible or conformable portion of ear canal engagement section 6635 may seal the ear canal. For example, ear canal engagement section 6635 includes stop 6630 that may be soft or flexible to conform to the entrance of the ear canal and thus, substantially seal the inside of the ear canal from pressure outside of the ear canal. As depicted in FIG. 66, the soft or flexible material is shaded to indicate the areas in which stop 6630 may conform around the outside of the ear canal to seal the inside of the canal.

In some embodiments, the diagnostic device may be used to visualize the eardrum while pressurizing the ear canal to observe for motion, the absence of motion, or indications of fluid behind the ear drum. Air outlet port 66135 of ear canal engagement section 6635 may limit the amount of pressure that can be created inside the ear canal to limit the potential for injury or discomfort. Air outlet port may have a pressure relief valve configuration to open once a certain pressure is reached within the ear canal.

In one embodiment, a method for obtaining diagnostic information includes using the diagnostic device, inserted into the ear canal of a human subject as described above, to obtain diagnostic information about the subject from the diagnostic elements. The diagnostic information can be communicated via communications circuitry in the device, e.g., to an external computing device for review.

Additional Considerations

In the foregoing disclosure, implementations of the disclosure have been described with reference to specific example implementations thereof. It will be evident that various modifications may be made thereto without departing from the broader spirit and scope of implementations of the disclosure as set forth in the following claims. Where the disclosure refers to some elements in the singular tense, more than one element can be depicted in the figures and like elements are labeled with like numerals. The disclosure and drawings are, accordingly, to be regarded in an illustrative sense rather than a restrictive sense.

As used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Where values are described as "approximate" or "substantially" (or their derivatives), such values should be construed as accurate +/−10% unless another meaning is apparent from the context. From example, "approximately ten" should be understood to mean "in a range from nine to eleven." In addition, use of the "a" or "an" are employed to describe elements and components of the embodiments. This is done merely for convenience and to give a general sense of the disclosure. This description should be read to include one or at least one and the singular also includes the plural unless it is obvious that it is meant otherwise.

What is claimed is:

1. A diagnostic device for obtaining diagnostic information about a human subject, the device comprising:
    an ear canal engagement section coupled to a body, and including:
        an insertion portion configured to be inserted into an ear canal of the human subject, the insertion portion having an upper portion and a lower sled portion that extends farther into the ear canal than the upper portion, and
        a stop extending from a top of the insertion portion of the ear canal engagement section; and
    a diagnostic extension protruding from the insertion portion and having one or more diagnostic elements for obtaining the diagnostic information, the diagnostic extension comprising an elastic material that facilitates conformance of the diagnostic extension to the ear canal when the diagnostic extension extends into the ear canal, the diagnostic extension extending further into the ear canal than the lower sled portion when the device is inserted into the ear canal and moving radially relative to the lower sled portion when contacting a wall of the ear canal.

2. The diagnostic device of claim 1, wherein the lower sled portion curves such that a distal end of the lower sled portion points towards a superior wall of the ear canal when of the lower sled portion points an inferior wall of the ear canal.

3. The diagnostic device of claim 1, wherein the lower sled portion is adapted such that the ear canal engagement section angles upward when of the lower sled portion points an inferior wall of the ear canal.

4. The diagnostic device of claim 1, further comprising:
a first portion and a second portion of the body, the second portion of the body including a cavity;
a first end of a post coupled to the second portion of the body at the cavity; and
an over ear piece configured to couple to the post.

5. The diagnostic device of claim 4, wherein a second end of the post is adapted to couple to the over ear piece.

6. The diagnostic device of claim 5, wherein a first end of the over ear piece comprises a cavity configured to receive the second end of the post, the surface of the cavity composed of a flexible material configured to expand around and compress onto the second end of the post.

7. The diagnostic device of claim 4, wherein the first portion of the body and the second portion of the body are coupled to one another at a flexible joint, wherein the flexible joint enables a first orientation of the body wherein the first portion of the body is orthogonal to the second portion of the body and a second orientation of the body wherein the first portion of the body is in line with the second portion of the body.

8. The diagnostic device of claim 1, wherein a height of the stop is approximately 25%-50% of a height of the ear canal engagement section.

9. The diagnostic device of claim 8, wherein the stop is flexible.

10. The diagnostic device of claim 8, wherein a width of the stop is no greater than a width of the ear canal engagement section.

11. The diagnostic device of claim 1, wherein a height of the ear canal engagement section at the proximal end of the body is greater than a height of the ear canal engagement section at the distal end of the of the body.

12. The diagnostic device of claim 1, wherein a height of the ear canal engagement section decreases in discrete steps.

13. The diagnostic device of claim 1, wherein the insertion portion further comprises a channel through which the diagnostic extension extends from the insertion portion, a height or width of the channel is greater than a height or width of the diagnostic extension, respectively.

14. The diagnostic device of claim 1, wherein a height of the ear canal engagement section is 5-13 millimeters.

15. The diagnostic device of claim 1, further comprising communications circuitry to wirelessly communicate the obtained diagnostic information to an external computing device.

16. The diagnostic device of claim 1, wherein the body further comprises an air injection button and an air outlet port configured to pressurize the ear canal.

17. The diagnostic device of claim 16, wherein the stop is configured to conform to the subject's ear outside of the ear canal to seal the ear canal.

18. The diagnostic device of claim 1, wherein the diagnostic extension comprises a tip housing a plurality of light sources and an imaging chip.

19. A method for obtaining diagnostic information about a human subject, the method comprising:
providing the diagnostic device of claim 1; and
receiving the diagnostic information from the one or more diagnostic elements of the diagnostic device.

* * * * *

UNITED STATES PATENT AND TRADEMARK OFFICE
CERTIFICATE OF CORRECTION

PATENT NO. : 12,390,161 B2  
APPLICATION NO. : 17/319042  
DATED : August 19, 2025  
INVENTOR(S) : Ryan Boucher et al.

Page 1 of 1

It is certified that error appears in the above-identified patent and that said Letters Patent is hereby corrected as shown below:

In the Claims

At Column 40, Claim 2, Line 62, delete "of"

At Column 40, Claim 2, Line 62, replace "points" with --contacts--

At Column 40, Claim 3, Line 66, delete "of"

At Column 40, Claim 3, Line 66, replace "points" with --contacts--

At Column 42, Claim 11, Line 2, delete one instance of the phrase "of the"

Signed and Sealed this  
Second Day of December, 2025

John A. Squires  
*Director of the United States Patent and Trademark Office*